(12) United States Patent  
Groman

(10) Patent No.: US 9,050,156 B2
(45) Date of Patent: Jun. 9, 2015

(54) SEALING PARTICULATE MATTER IN A MICRO-ABRASIVE BLASTING DEVICE

(76) Inventor: Boaz Barry Groman, Boca Raton, FL (US)

(*) Notice: Subject to any disclaimer, the term of this patent is extended or adjusted under 35 U.S.C. 154(b) by 767 days.

(21) Appl. No.: 13/190,479

(22) Filed: Jul. 26, 2011

(65) Prior Publication Data

US 2011/0281239 A1   Nov. 17, 2011

Related U.S. Application Data

(60) Continuation-in-part of application No. 12/551,416, filed on Aug. 31, 2009, now Pat. No. 8,241,094, which is a division of application No. 11/452,067, filed on Jun. 13, 2006, now Pat. No. 7,607,972, application No. 13/190,479, which is a continuation-in-part of application No. 13/083,532, filed on Apr. 9, 2011, now Pat. No. 8,360,826, which is a continuation of application No. 12/764,939, filed on Apr. 21, 2010, now Pat. No. 7,927,188, which is a division of application No. 11/077,098, filed on Mar. 10, 2005, now Pat. No. 7,731,570.

(51) Int. Cl.
*B24C 5/02* (2006.01)
*A61C 3/025* (2006.01)
*B24C 7/00* (2006.01)
*A61B 17/54* (2006.01)

(52) U.S. Cl.
CPC .............. *A61C 3/025* (2013.01); *A61B 17/545* (2013.01); *B24C 7/0053* (2013.01); *B24C 7/0069* (2013.01)

(58) Field of Classification Search
CPC ............... B24C 5/04; B24C 5/02; B24C 1/00
USPC ................ 451/38, 39, 40, 90, 99, 102
See application file for complete search history.

(56) References Cited

U.S. PATENT DOCUMENTS

| 2,133,149 | A | | 10/1938 | Poncelet |
| 2,441,441 | A | * | 5/1948 | Paasche ........................ 451/90 |
| 2,577,465 | A | | 12/1951 | Jones et al. |
| 2,612,732 | A | | 10/1952 | Ziegler |
| 2,641,087 | A | | 6/1953 | Greiser |

(Continued)

FOREIGN PATENT DOCUMENTS

GB   832231   4/1960

OTHER PUBLICATIONS

Airbrator User Instructions, 3 pages.

(Continued)

*Primary Examiner* — Robert Rose
(74) *Attorney, Agent, or Firm* — Gerald E. Linden

(57) ABSTRACT

A micro-abrasive blasting device comprises a mixing chamber, a delivery conduit extending from external the mixing chamber to the mixing chamber and a discharge conduit extending from the mixing chamber. Embodiments having delivery and discharge conduits extending from the same, or from opposite ends of the mixing chamber are disclosed. Abrasive material may selectively be sealed in the chamber by positioning the discharge conduit to abut the inlet port. Other sealing techniques are disclosed, such as capping or plugging the delivery and discharge conduits. The chamber may be spherical to deliver consistent powder perturbation at all mixing chamber orientations. Methods of using the device are disclosed. Methods of making the device by blow molding are disclosed.

19 Claims, 13 Drawing Sheets

(56) References Cited

U.S. PATENT DOCUMENTS

| | | |
|---|---|---|
| 2,696,049 A | 12/1954 | Black |
| 2,696,669 A | 12/1954 | Ikse |
| 2,725,684 A | 12/1955 | Crowe |
| 2,744,361 A | 5/1956 | Larson et al. |
| 3,164,153 A | 1/1965 | Zorzi |
| 3,626,841 A | 12/1971 | Schachter |
| 3,631,631 A | 1/1972 | Greenstein |
| 3,964,509 A | 6/1976 | Daubenberger et al. |
| 3,981,479 A | 9/1976 | Foster et al. |
| 4,032,474 A | 6/1977 | Goudriaan et al. |
| 4,174,571 A | 11/1979 | Gallant |
| 4,287,812 A | 9/1981 | Iizumi |
| 4,369,607 A | 1/1983 | Bruggemann et al. |
| 4,391,590 A | 7/1983 | Dougherty |
| 4,475,370 A | 10/1984 | Stark et al. |
| 4,646,782 A | 3/1987 | Ezekoye |
| 4,673,051 A | 6/1987 | Darling et al. |
| 4,941,298 A | 7/1990 | Fernwood et al. |
| 4,967,791 A | 11/1990 | Sternberger |
| 5,123,206 A | 6/1992 | Woodson |
| 5,160,547 A | 11/1992 | Kirschner et al. |
| 5,197,876 A | 3/1993 | Coston |
| 5,199,229 A | 4/1993 | Herold |
| 5,261,459 A | 11/1993 | Atkinson et al. |
| 5,289,919 A | 3/1994 | Fischer |
| 5,330,354 A | 7/1994 | Gallant |
| 5,356,292 A | 10/1994 | Ho |
| 5,368,844 A | 11/1994 | Gaffar et al. |
| 5,839,946 A | 11/1998 | Hertz |
| 6,004,191 A | 12/1999 | Schur et al. |
| 6,024,566 A | 2/2000 | Bruns et al. |
| 6,083,001 A | 7/2000 | Deardon et al. |
| 6,093,021 A | 7/2000 | Rainey |
| 6,099,306 A | 8/2000 | Lawler |
| 6,287,180 B1 | 9/2001 | Hertz |
| 6,293,856 B1 * | 9/2001 | Hertz et al. ............... 451/90 |
| 6,343,717 B1 | 2/2002 | Zhang et al. |
| 6,347,984 B1 | 2/2002 | Groman |
| 6,354,924 B1 | 3/2002 | Trafton et al. |
| 6,398,628 B1 | 6/2002 | Groman |
| 6,439,966 B2 * | 8/2002 | Bruns et al. ............... 451/38 |
| 6,485,304 B2 | 11/2002 | Beerstecher et al. |
| 6,951,505 B2 | 10/2005 | Hertz |
| 7,101,265 B1 | 9/2006 | Schur et al. |
| 7,226,342 B2 | 6/2007 | Hertz |
| 7,607,972 B2 | 10/2009 | Groman |
| 7,731,570 B2 | 6/2010 | Groman |
| 2002/0077041 A1 | 6/2002 | Groman |
| 2003/0003849 A1 | 1/2003 | Groman |
| 2006/0205330 A1 | 9/2006 | Groman |
| 2006/0252006 A1 | 11/2006 | Apelker et al. |
| 2007/0287126 A1 | 12/2007 | Groman |
| 2009/0317759 A1 | 12/2009 | Groman |
| 2010/0086893 A1 | 4/2010 | Groman |
| 2010/0203804 A1 | 8/2010 | Groman |

OTHER PUBLICATIONS

Prepmaster User Instructions, copr 2004.
Air Abrasion Industry, copr 2003.

* cited by examiner

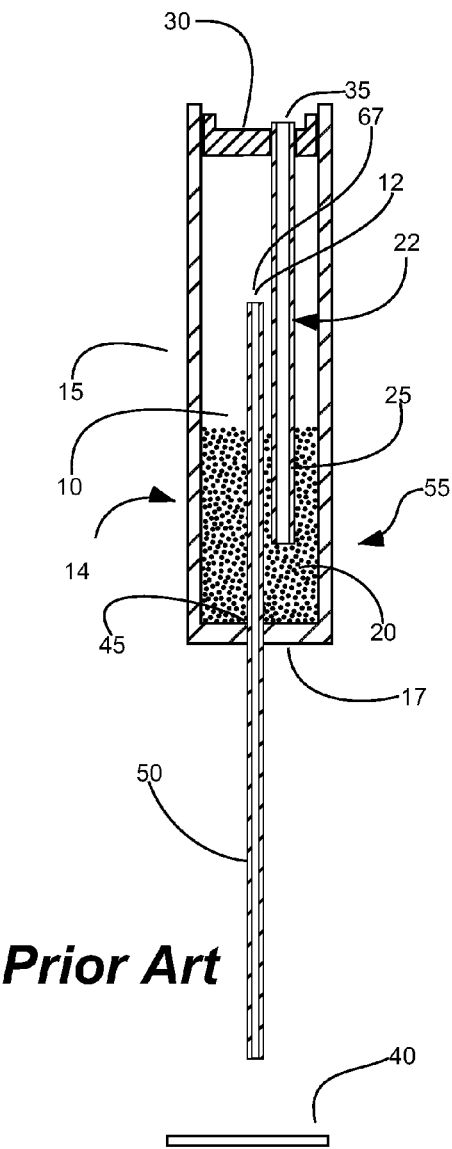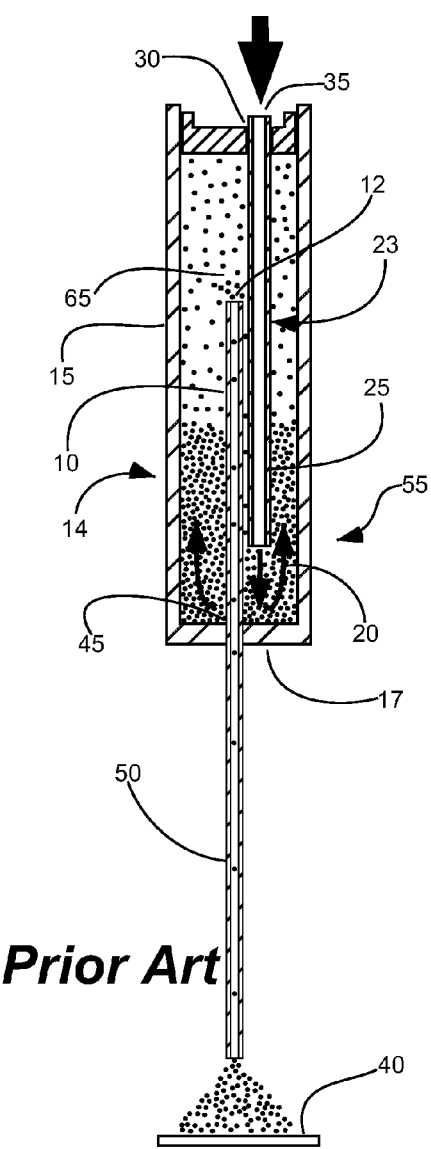
Prior Art
FIG. 1A
Prior Art
FIG. 1B

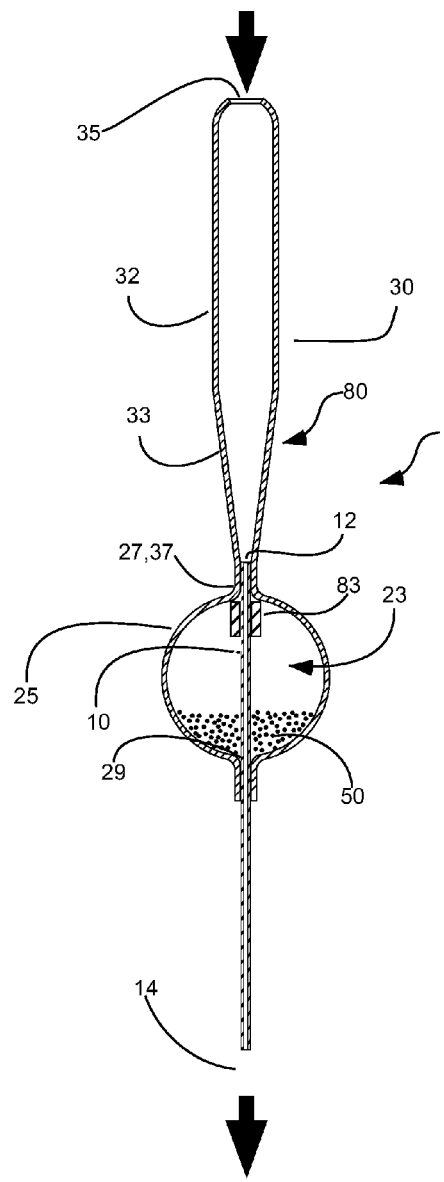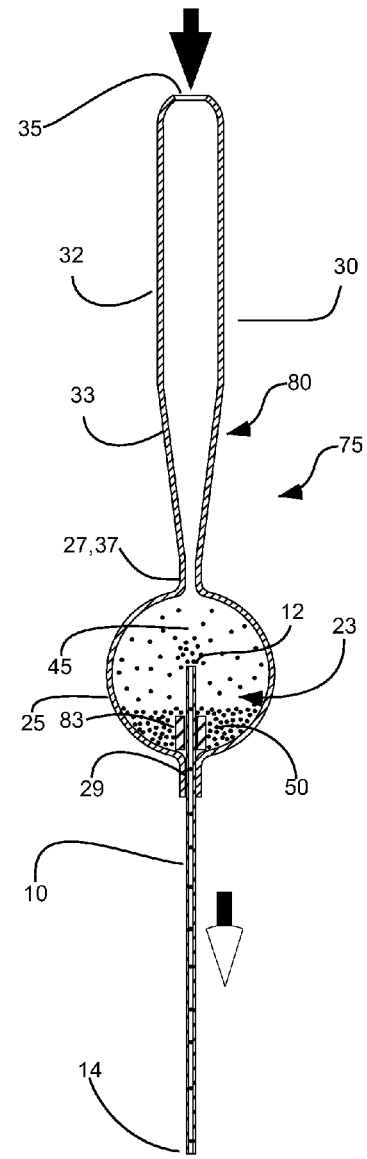
*FIG. 5A*    *FIG. 5B*

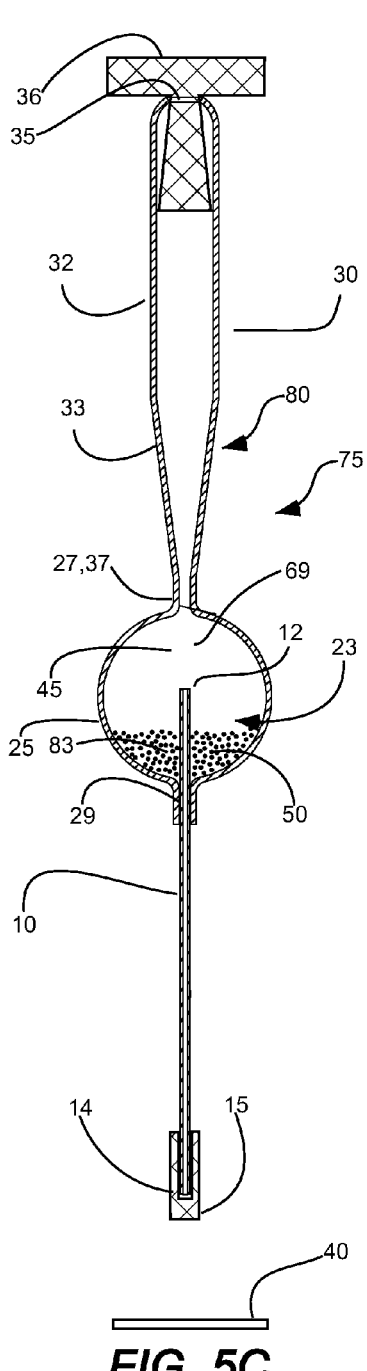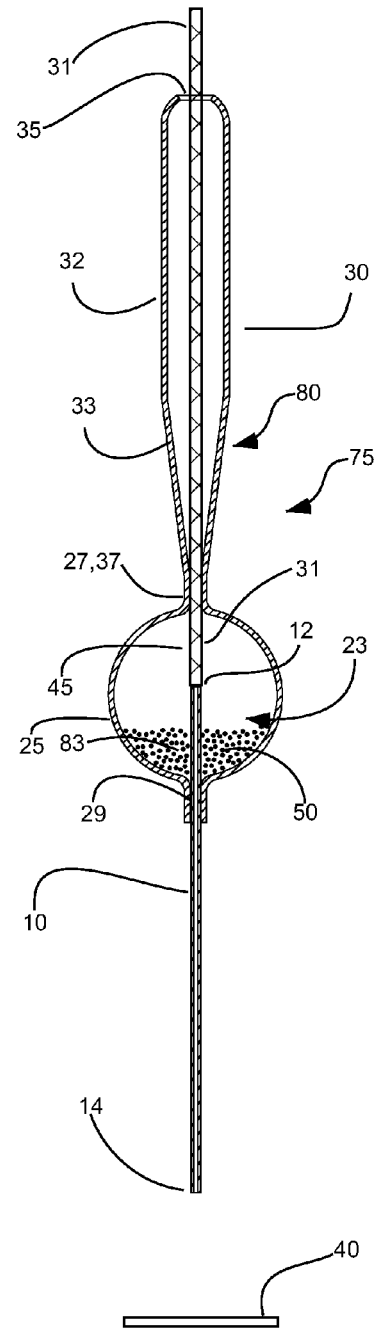
FIG. 5C
FIG. 5D

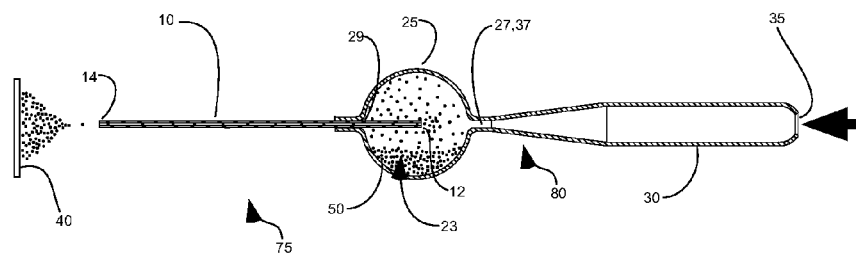
*FIG. 6A*
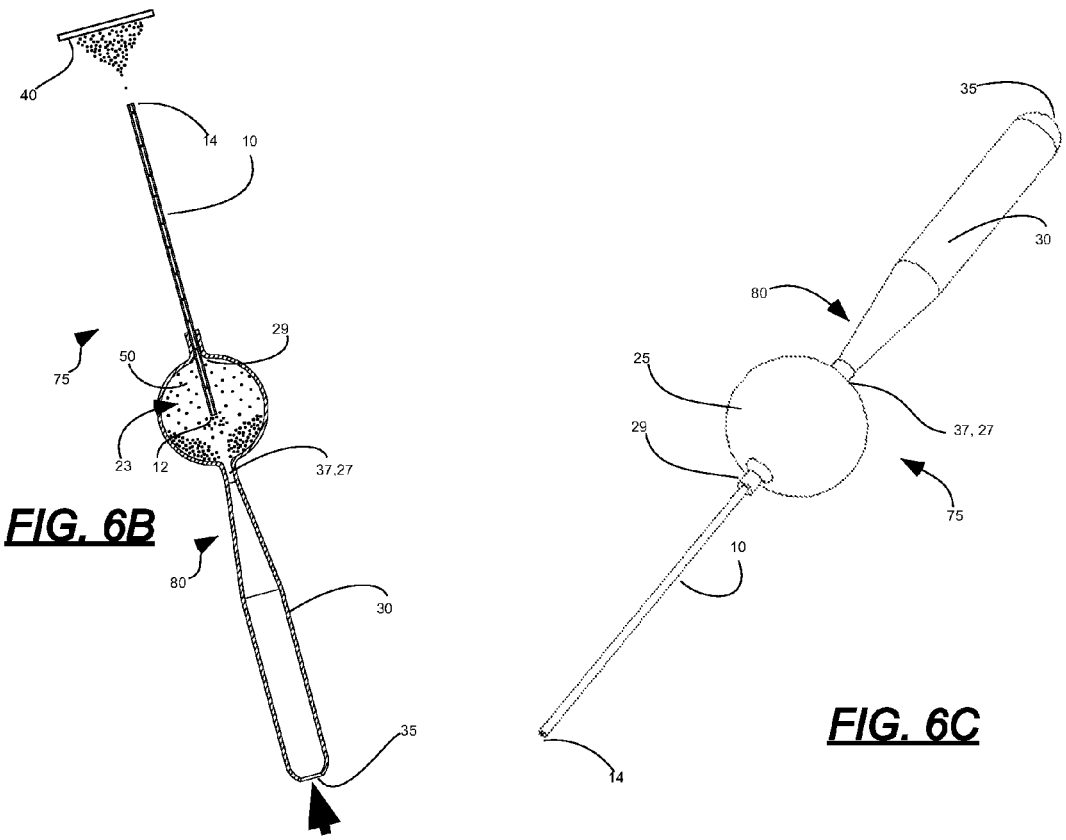
*FIG. 6B*
*FIG. 6C*

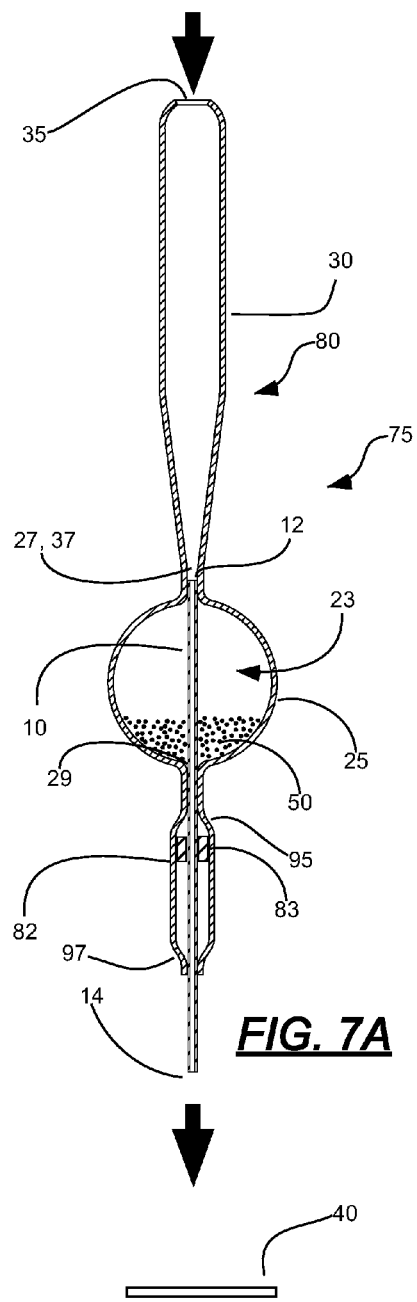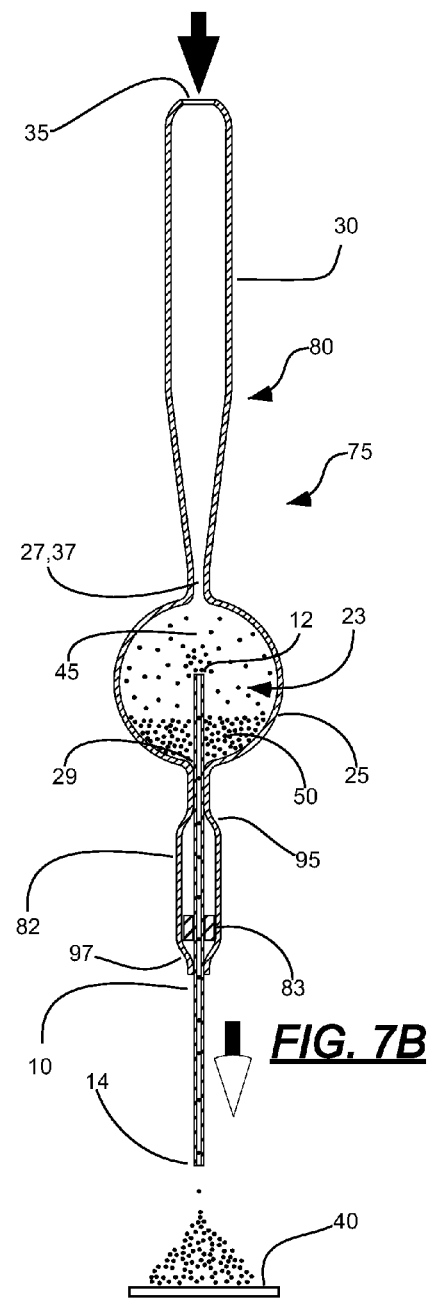

closed (sealed), no air flow through device open (unsealed), air flows through device

SEALING PARTICULATE MATTER IN A MICRO-ABRASIVE BLASTING DEVICE

CROSS-REFERENCE TO RELATED APPLICATIONS

This is a continuation-in-part of U.S. Ser. No. 12/551,416 filed Aug. 31, 2009 (now U.S. Pat. No. 8,241,094 issued Aug. 14, 2012) which is a division of U.S. Ser. No. 11/452,067 filed Jun. 13, 2006 (now U.S. Pat. No. 7,607,972 issued Oct. 27, 2009).

This is a continuation-in-part of U.S. Ser. No. 13/083,532 filed Apr. 9, 2011 (now U.S. Pat. No. 8,360,826 issued Jan. 29, 2013) which is a continuation of U.S. Ser. No. 12/764,939 filed Apr. 21, 2010 (now U.S. Pat. No. 7,927,188 issued Apr. 19, 2011) which is a division of U.S. Ser. No. 11/077,098 Mar. 10, 2005 (now U.S. Pat. No. 7,731,570 issued Jun. 8, 2010).

FIELD

The invention relates generally to devices for propelling abrasive powder for etching a surface of a target material and, more particularly, micro-abrasive blasting devices powered by a pressurized-gas source for use with dental procedures, and features thereof.

BACKGROUND

Abrasive blasting devices operate on the physical property that gas at a higher pressure flows towards and into gas at lower pressure. When abrasive powder is mixed with gas at higher pressure, the gas carries the abrasive powder as the gas accelerates and flows to the lower pressure. As the gas and abrasive powder blast the target material at high speed, the impact of the particles removes layers of the target material. In dentistry this technology is known as micro-abrasion and is used to achieve a variety of goals—such as to remove foreign material or to dull a shiny surface, roughen or etch the surface to enhance bonding quality and to remove decay by drilling and cutting tooth structure.

Air abrasion devices are disclosed in U.S. Pat. No. 2,612,732 (Ziegler), U.S. Pat. No. 2,725,684 (Crow), U.S. Pat. No. 3,626,841 (Schachter) and U.S. Pat. No. 2,441,441 (Paache), and fall into two main categories: (i) providing a separate mixing apparatus for generating the abrasive laden air stream and delivering the abrasive laden air stream through an extended hand-piece for directing the stream onto the target surface, and (ii) integrating the mixing apparatus into the hand-held device.

The first category of devices facilitate more complex mechanisms and many operational options since the size and weight of the device are of no concern. Because the extended hand-piece delivers the abrasive laden air stream independent of the mixing operation, the hand-piece can be held at any orientation during operation. U.S. Pat. No. 6,083,001 (Deardon et al.) discloses a dental air abrasion system in which the flow of the particles is electronically controlled by pressure differentials. U.S. Pat. No. 6,093,021 (Rainey) discloses an automated control system which utilizes a gas stream mounted particulate sensor to regulate fluid flow rates into and around the ultrasonically agitated mixing chamber in order to accurately maintain the abrasive concentration in the air stream. Various methods for reducing the overspray of the abrasive have also been developed for these devices. U.S. Pat. No. 5,356,292 (Ho), U.S. Pat. No. 5,197,876 (Coston), and U.S. Pat. No. 6,024,566 (Burns et al.) disclose add-on splatter guard and collector attachments to air abrasion devices.

In the second category, the size, weight, and ergonomic shape of the device are significant factors. U.S. Pat. No. 5,199,299 (Herald et al.) and U.S. Pat. No. 6,439,966 (Burns et al.) disclose innovative hand-holdable air abrasion devices which mount the mixing apparatus into the hand-piece. The drawback of this approach is that the operation of these devices is limited by the orientation of the mixing chamber. An adjunct to the second category of devices has been the concept of simple self-contained air abrasion devices—such as U.S. Pat. No. 5,839,946 (Hertz), U.S. Pat. No. 6,287,180 (Hertz), U.S. Pat. No. 6,951,505 (Hertz), and U.S. Pat. No. 7,226,342 (Hertz), U.S. Pat. No. 6,398,628 (Groman), U.S. Pat. No. 6,347,984 (Groman), Schur et al. U.S. Pat. No. 6,004,191, and U.S. Pat. No. 6,354,924 (Trafton et al.). These devices rely on the air stream to perturb the abrasive and generate the mixing action based on U.S. Pat. No. 4,475,370 (Stark et al.) fixed air abrasion device for treating dental castings.

Merging of Stark's blow-through mixing method into the hand-piece so the mixing chamber is held between the user's fingers has taken air abrasion art to a new level. Because of their simplified structures, simple self-contained air abrasion devices tend to be less expensive to manufacture and can therefore be marketed to the user as disposable instruments.

With increased emphasis in Medical, Pharmaceutical, Cosmetic and Dental applications on reduced cross-patient contamination, there has been a significant drive towards single usage disposable packaging and devices. With advances in materials and fabrication technologies the cost of these devices has been significantly reduced. U.S. Pat. No. 4,391,590 (Dougherty) discloses a syringe and stopper like cartridge device for dispensing material while U.S. Pat. No. 5,839,946 (Hertz) discloses the formulation an air abrasion instrument from a syringe and stopper type structure. Both innovations capitalize on the lower cost of fabrication and the well established production methods of a syringe and stopper configuration.

Simple self-contained prior art air abrasion devices support an elongated cylindrical chamber with an inlet conduit for delivering the air into the mixing chamber and a discharge conduit for carrying the air-abrasive mixture out of the mixing chamber. The mixing chambers are utilized as a reservoir for storing the abrasive powder. Once the reservoir is depleted of abrasive material, the devices are discarded and therefore function as disposable instruments which do not require sterilization post intra-oral use.

To prevent the abrasive material from escaping the mixing chamber or becoming contaminated prior to use, simple self-contained prior art air abrasion devices add additional components which seal the inlet and outlet ports and conduits. While the U.S. Pat. No. 5,839,946 (Hertz), and U.S. Pat. No. 6,004,191 (Schur et al.) devices include passive caps which must be removed prior to using the instrument, U.S. Pat. No. 6,951,505 (Hertz) and U.S. Pat. No. 6,287,180 (Hertz), and U.S. Pat. No. 6,398,628 (Groman) and U.S. Pat. No. 6,347,984 (Groman) add functional components which actively prevent the abrasive from exiting the mixing chamber. U.S. Pat. No. 6,398,628 (Groman) discloses a filter that prevents the abrasive from exiting the device's inlet port and a movable discharge conduit which prevents abrasive material from exiting the mixing chamber when the discharge conduit inlet port abuts the side wall of the mixing chamber. U.S. Pat. No. 6,951,505 (Hertz) has a deformable seal at the inlet port external to the mixing chamber which functions as a check-valve that allows the pressurized-gas to enter the instrument but prevents abrasive from exiting the instrument. U.S. Pat. No. 6,398,628 (Groman) discloses a deformable and movable cap configurations which block both the delivery conduit inlet and discharge conduit outlet prior to use.

Another disposable delivery method disclosed by U.S. Pat. No. 6,343,717 (Zhang et al.) attempts to address the containment of stored material utilizing a pipette structure. A typical pipette consists of a slender pipe or tube that is used to transfer or measure small quantities of material from one location to another. The most common type of pipette consists of a small tube that widens into a bulb at the middle. The Zhang et al. pipette structure is made of a rigid or resilient material that is pre-filled with a pharmaceutical or cosmetic product and is used once and then discarded. Zhang et al. discloses a plurality of ways by which the disposable pipette can be sealed to contain the material and then unsealed by the user prior to use for dispensing the stored material. According to Zhang's et al. invention the majority of material is retained within the bulb section of the pipette, but Zhang's et al. sealing methods permit the contained material to migrate into the top and bottom tube sections. Although Zhang's et al. use of a pipette structure leads to a very cost effective means of delivering the contained material, Zhang's et al. sealing methods are not compatible with the needs of air abrasion devices.

Pressurized air stream is delivered to the simple self-contained air abrasion devices of Hertz, Groman, Schur, and Trafton via custom connectors which engage the device externally and to form a seal with the device body to deliver the pressurized air to the mixing chamber delivery port. The connectors are designed to supply clean dry air in order to maintain the abrasive powder dry, since any moisture causes clumping of the abrasive material and therefore the malfunction of the device. The dry air is required because the gas delivery conduit leads directly into the mixing chamber; therefore any liquid present at the entry to the device gets trapped in the mixing chamber. U.S. Pat. No. 6,293,856 (Hertz et al.) discloses a connector with additional conduits for carrying other types of fluids passively through the mixing chamber. This configuration requires a very complex connector to assure the separation of the fluids delivered to the air abrasion instrument without contaminating the mixing chamber. Custom connectors which supply dry air add to the installation cost and complexity of these disposable devices. And because they attach to the body of the devices, these connectors are typically very bulky.

Referring to FIGS. 1A, 1B, prior art self-contained air abrasion devices use a blow-through methodology to agitate the abrasive powder. More specifically, these devices utilize the delivery conduit to deliver the gas stream into the abrasive material. As the gas stream blows through the abrasive material, the abrasive material is agitated. Gravity is utilized to assure that the non-aerated abrasive remains at the bottom of the mixing chamber. As the air stream reverses direction towards the discharge conduit inlet, aerated particles are captured by the air stream. The abrasive laden air stream is pushed out of the mixing chamber through the discharge conduit by the higher pressure gas source.

In their reduction to practice, both the Schur and Groman devices require the user to maintain the orientation of the device so the mixing chamber points downward. The attached user instructions for the Schur and Groman devices outline the specific user instructions cautioning the user about misorienting the mixing chamber. To compensate for his shortcoming, the marketed Groman instrument provides a finger bendable discharge conduit. The marketed Schur device provides a bending tool, so the user is able to form the delivery conduit to reach upper surfaces while maintaining the proper orientation of the mixing chamber.

Referring to FIG. 2, if the user attempts to utilize these prior art devices with the mixing chamber horizontal or upside down, the abrasive material is pushed directly into the discharge conduit without being properly mixed with the air steam. This leads to a concentration of abrasive material to exit the device in an uncontrolled manner, which creates a cloud of abrasive dust or clogs up the discharge conduit as the abrasive powder binds. Additionally, in certain orientations the delivery conduit is not immersed in the abrasive material which also disrupts the mixing operation of these prior art devices. In fact, the pressurized-gas exiting the delivery conduit creates a back pressure on the abrasive within the mixing chamber causing the abrasive powder particles to bind together instead of mix with the air stream. Most importantly, these disruption in flow can lead to a defective clinical procedure which either under or over etches the target tooth surface.

SUMMARY

Various embodiments of the invention disclosed herein may address and resolve shortcomings of the prior art, such as:

eliminating the need for the inlet and outlet caps or other sealing methods.

making the device insensitive to liquids at the pressurized-gas connection.

making the air abrasive mixing operation independent of the orientation of the mixing chamber.

eliminating back pressure buildup within the mixing chamber.

eliminating the need for a bulky custom connection to the instrument for pressurized-gas delivery.

The air abrasion device disclosed herein may be made of a continuous tubing formed into a disposable pipette structure. Accordingly, some objects and advantages of the present invention may include:

reducing component count by utilizing the discharge conduit in conjunction with the delivery conduit inlet to seal the abrasive material within the mixing chamber.

creating a bypass to the mixing chamber so liquids in the pressurized-gas connection are purged out of the system without contaminating the abrasive within the mixing chamber.

providing a spherical mixing chamber which assures a distal separation between the discharge conduit inlet and the abrasive powder at all mixing chamber orientations.

eliminating the air stream reversal within the mixing chamber so back pressure is never created on the abrasive powder.

extending the delivery conduit external to the mixing chamber so a slender handheld gas supply connector and standard tube fittings can be utilized for pressurized-gas delivery.

making the disposable pipette structure usable for air abrasion applications in order to further reduce the manufacturing costs.

Another object of the invention may include that the material in the bulb of the pre-filled pipette may be protected from contamination or spillage by the discharge conduit.

In an embodiment of the invention, a micro-abrasive blasting device constructed from a disposable pipette structure comprising a delivery conduit extending from a delivery conduit inlet through a tapered section to form a delivery conduit outlet and a inlet port; contiguous pipette structure expands from inlet port to form a hollow bulb mixing chamber and then narrows to form a discharge port section; a discharge conduit is in fluid communications with discharge port and extends from a discharge conduit inlet internal to mixing chamber to a discharge conduit outlet external to mixing chamber; a particulate matter is disposed within mixing chamber wall; discharge conduit inlet abuts inlet port preventing particulate matter from exiting mixing chamber. A separation gap between the delivery conduit outlet and discharge conduit inlet is created as discharge conduit is displaced so discharge conduit inlet no longer abuts inlet port; As pressurized-gas is supplied to micro-abrasive blasting device through the delivery conduit inlet, the pressurized-gas flows through the delivery conduit and out of the inlet port, into mixing chamber. As flow is initiated, particulate matter instantaneously mixes with the gas-steam within hollow resilient bulb mixing chamber and the powder-gas mixture flows through discharge conduit to strike target surface.

In an embodiment of the invention, the discharge conduit has a U-shaped portion internal to the mixing chamber, and the device may be unsealed by pushing the discharge conduit into the mixing chamber (rather than pulling it out, as in other embodiments). The delivery conduit may also be U-shaped so as to terminate at the same wall of the chamber as the discharge conduit.

BRIEF DESCRIPTION OF THE DRAWINGS

Various other objects, advantages, and features of the invention will become apparent to those skilled in the art from the following discussion taken in conjunction with the following drawings, where closely related figures have the same number but different alphabetic suffixes:

FIGS. 1A, 1B and FIG. 2 are cross-sectional views of prior art micro-abrasive blasting devices.

FIGS. 5A, 5B are isometric and cross-sectional views of micro-abrasive blasting devices with a spherical mixing chamber, according to an embodiment of the invention.

FIG. 5C is a perspective show showing a micro-abrasive device with removable end closure elements such as plugs or caps on its delivery and discharge conduits.

FIG. 5D is a perspective show showing a micro-abrasive device with a removable elongate element extending through the delivery conduit to seal the discharge conduit inlet 12 of the discharge conduit 10.

FIGS. 6A, 6B, 6C are isometric and cross-sectional views of micro-abrasive blasting devices with a spherical mixing chamber, according to an embodiment of the invention.

FIGS. 7A, 7B are cross-sectional views of an embodiment of the micro-abrasive blasting device with discharge conduit bearing integral to the pipette structure.

Figure 2:
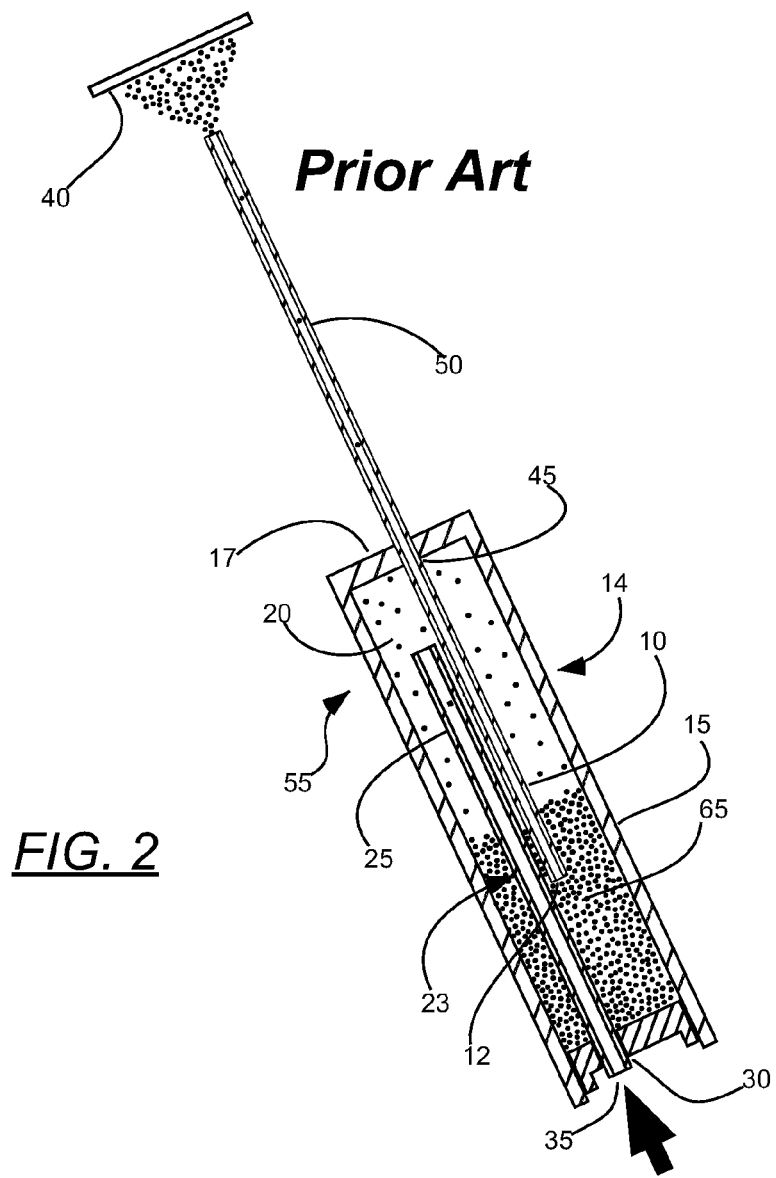

REFERENCE NUMERALS IN DRAWINGS 10 discharge conduit
12 discharge conduit inlet
14 discharge conduit outlet
15 discharge conduit outlet closure element (cap)
23 mixing chamber
25 mixing chamber wall
27 inlet port
29 discharge port
30 delivery conduit
31 rod extending through the delivery conduit
32 delivery conduit external section
33 delivery conduit tapered section
34 delivery conduit internal section
35 delivery conduit inlet
36 delivery conduit inlet closure element (plug)
37 delivery conduit outlet
40 target surface
45 separation gap
48 pressure gradient
50 particulate matter
55 handheld supply connector
75 micro-abrasive blasting device
80 pipette structure
82 discharge conduit bearing
83 Discharge conduit stop
85 protective nozzle guard
87 nozzle guard separation point
90 particle deflector
93 particle deflector separation point
95 capped position end
97 mixing position end

DETAILED DESCRIPTION

It should be understood that the disclosed embodiments are merely exemplary of the invention, which may be embodied in various forms. Therefore, specific structural and functional details disclosed herein should not be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES (FIGs.) are designated by the same reference numerals. Various embodiments will be described.

An Embodiment

Referring to FIGS. 3A, 3B, 3C, 3D, a micro-abrasive blasting device 75 is disclosed. Micro-abrasive blasting device 75 comprises a mixing chamber 23 formed by a mixing chamber wall 25 and supports an inlet port 27 and a discharge port 29; a delivery conduit 30 extending from a delivery conduit inlet 35 external to mixing chamber 23 to a delivery conduit outlet 37 internal to mixing chamber 23, by means of protruding into mixing chamber 23 through mixing chamber wall 25 at inlet port 27; a discharge conduit 10 is in fluid communications with mixing chamber 23 at discharge port 29, and extending from a discharge conduit inlet 12 internal to mixing chamber 23 to a discharge conduit outlet 14 external to mixing chamber 23; a particulate matter 50 is disposed within mixing chamber 23.

Delivery conduit 30 comprises a delivery conduit external section 32 external to mixing chamber 23 and a delivery conduit internal section 34 internal to mixing chamber 23 and a connecting delivery conduit tapered section 33; external section 32 of delivery conduit 30 may be straight and may support an outer and inner diameter that fits into standard tube and hose connectors such as push-in or push-on connector types; internal section 34 of delivery conduit 30 may support an inner diameter that is equivalent to the outer diameter of discharge conduit inlet 12.

Figure 3A:
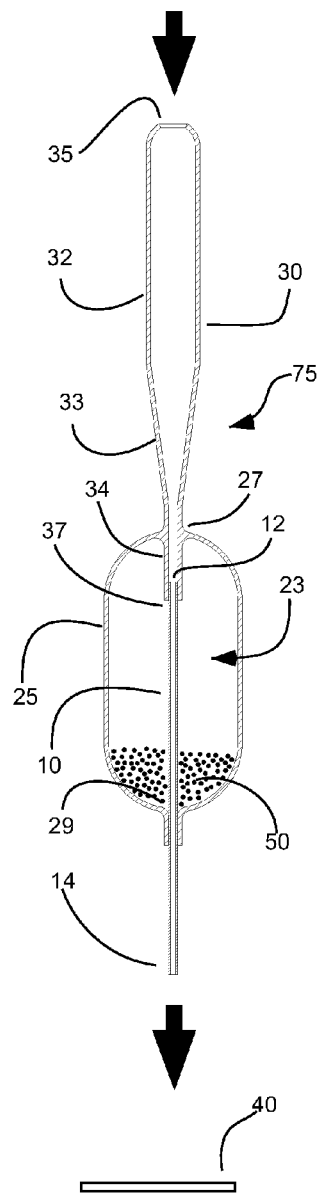
FIGS. 3A, 3B, 3C are cross-sectional views of a micro-abrasive blasting device and isometric view of the device mounted into a handpiece connector, according to an embodiment of the invention.
Figure 3B:
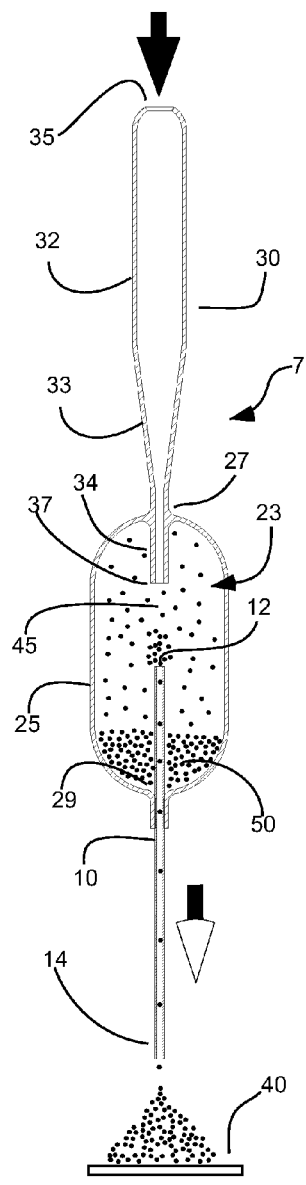
Figure 3C:
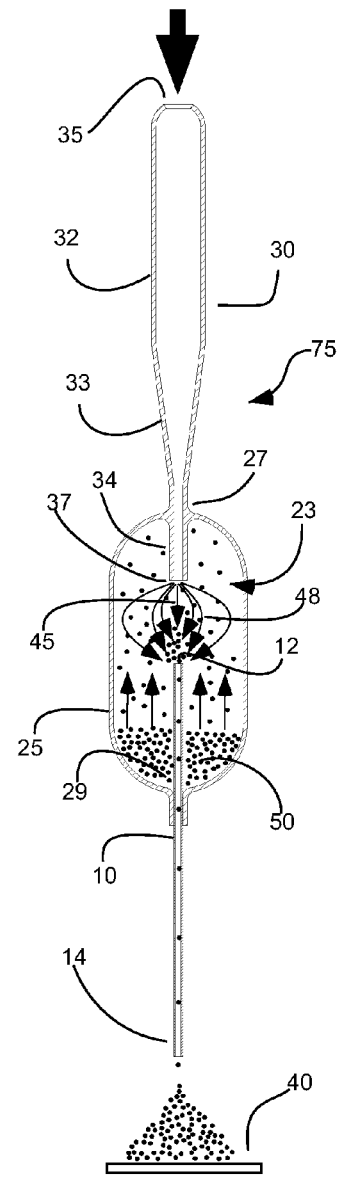
Figure 3D:
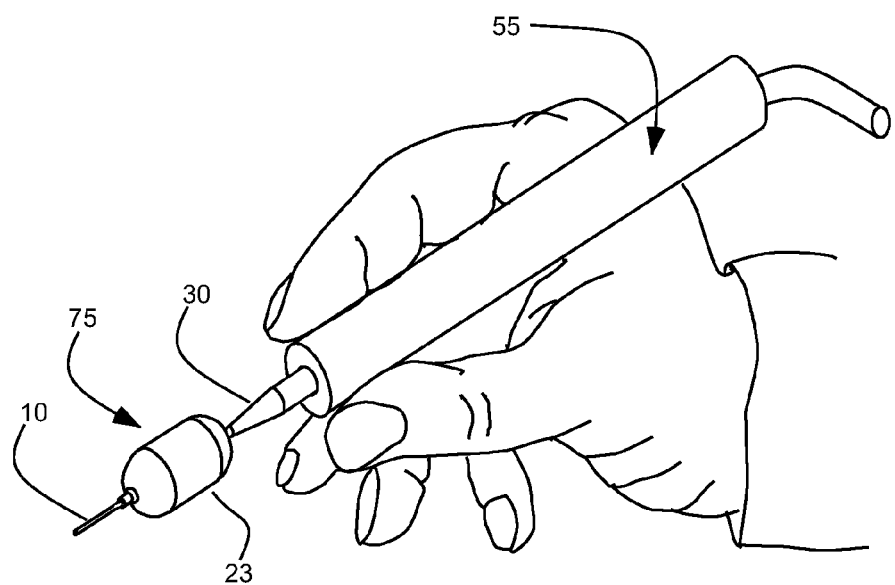
FIG. 3D is a perspective view showing a micro-abrasive blasting device in use, according to an embodiment of the invention.

Referring to FIG. 3D, extending delivery conduit 30 external to the mixing chamber 23 facilitates a connection to a handheld pressurized-gas supply connector 55. Not only does this innovative configuration simplify the type of connection required for supplying the pressurized-gas and therefore the cost of the air supply adaptor, it also facilitates a more narrow connection to the air abrasion device. Whereas, prior art devices connect to the mixing chamber body, this embodiment connects to a narrower delivery conduit. Therefore, the innovative micro-abrasive blasting device 75 may be mounted as a disposable tip onto a non-disposable handheld supply connector 55. While handheld supply connector 55 is held by the user's fingertips, delivery conduit 30 of micro-abrasive blasting device 75 mounts into handheld supply connector 55 downstream of the user's fingertips. Because the innovative micro-abrasive blasting device 75 does not support the user's grip and bulky supply connector, micro-abrasive blasting device 75 can be made shorter and of less rigid material. This configuration greatly decreases the complexity and cost of the micro-abrasive blasting device 75.

Referring to FIG. 3A, discharge conduit inlet 12 abuts delivery conduit outlet 37 as to prevent particulate matter 50 from exiting mixing chamber 23, thereby sealing particulate matter 50 within mixing chamber 23. As delivery conduit external section 32 engages with a pressurized-gas source, pressurized-gas is delivered to delivery conduit 30 at delivery conduit inlet 35; the pressurized-gas passes through delivery conduit 30 into discharge conduit 10 to exit micro-abrasive blasting device 75 at discharge conduit outlet 14. Since discharge conduit inlet 12 abuts delivery conduit outlet 37 the pressurized gas can not enter mixing chamber 23.

Therefore, any moisture or liquid residue contained in or carried by the pressurized-gas does not enter mixing chamber 23 and is discharged through micro-abrasive blasting device 75.

Referring to FIG. 3B, a separation gap 45 between the delivery conduit outlet 37 and discharge conduit inlet 12 is created as discharge conduit 10 is displaced so discharge conduit inlet 12 no longer abuts delivery conduit outlet 37; As pressurized-gas is supplied to micro-abrasive blasting device 75 through delivery conduit inlet 35, the pressurized-gas flows through delivery conduit 30 and out of delivery conduit outlet 37 into mixing chamber 23. When gas flow is present, particulate matter 50 instantaneously mixes with the flowing gas and is dispensed through discharge conduit 10 to strike target surface 40. Once mixing chamber 23 is depleted of particulate matter 50, micro-abrasive blasting device 75 is removed from the pressurized-gas source and discarded.

Another Embodiment

Figures 4A, 4B:
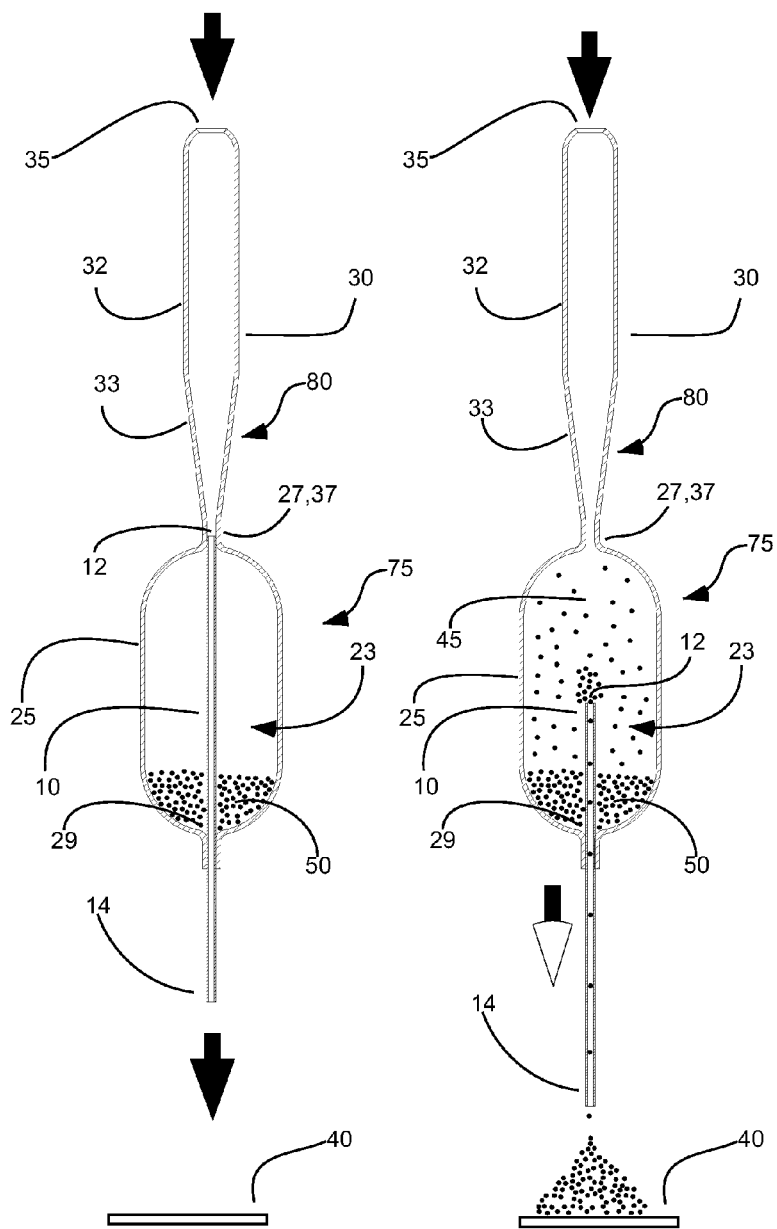
FIGS. 4A, 4B are cross-sectional views of a micro-abrasive blasting device fabricated out of a pipette structure, according to an embodiment of the invention.

Referring to FIGS. 4A, 4B, a micro-abrasive blasting device 75 is comprised of a hollow resilient round tubular pipette structure 80 constructed of a thermoplastic material such as polycarbonate, polyethylene, polyester, polystyrene, polypropylene, polysulfone, polyurethane, ethylene-vinyl-acetate or the like. The material may be transparent, translucent, opaque, or pigmented to indicate the type of abrasive powder contained within the sealed mixing chamber. Pipette structure 80 may have a circular cross section but can also be fabricated out of other cross sectional shapes.

Micro-abrasive blasting device 75 is comprised of a pipette structure 80 which consists of three sections, a hollow bulb section forming a mixing chamber 23; a open ended hollow tubular delivery conduit 30 section smaller in diameter and contiguous with the bulb section at inlet port 27, for delivery of pressurized-gas; a hollow tubular discharge port 29 section smaller in diameter and contiguous with the bulb section, for discharging abrasive laden gas stream; a discharge conduit 10 in fluid communications with discharge port 29, and extending from a discharge conduit inlet 12 internal to mixing chamber 23 to a discharge conduit outlet 14 external to mixing chamber 23; a particulate matter 50 is disposed within mixing chamber 23. Delivery conduit 30 section may extend from a delivery conduit inlet 35 through a external section 32 and a tapered section 33 to form a delivery conduit outlet 37 and a inlet port 27.

The outer and/or inner diameter of delivery conduit external section 32 may be selected to fit standard tube or hose fittings, while the inner diameters of inlet port 27 and discharge port 29 may support an inner diameter that is equivalent to or less than the outer diameter of discharge conduit 10. Design selections of these diameters may eliminate or reverse the gradient of delivery conduit tapered section 33, rendering delivery conduit 30 a straight tube. The diameter of hollow resilient bulb mixing chamber 23 may be selected to support the appropriate quantity of particulate matter 50 to at least perform one dental procedure.

Pipette structure 80 may be formed via blow-molding and/or tube swaging techniques, or other thermo-forming processes. These methods would typically require that one of the ends of the tubular pipette structure 80 be sealed in order to entrap pressurized-gas for forming the component during the blow-molding process. The sealed end may be formed at the delivery conduit inlet 35 of delivery conduit 30 section or at the tip of discharge port 29 section. The sealed end may be trimmed off during the assembly process of micro-abrasive blasting device 75 or just punctured or cut to permit air flow into micro-abrasive blasting device 75 when mounted onto a pressurized-gas connector. Additionally, the pressurized-gas connector could support cutting or puncturing means for breaking the blow-molded seal when delivery conduit 30 is mounted on the pressurized-gas connector.

Referring to FIG. 4A, discharge conduit inlet 12 fits within or abuts inlet port 27 preventing particulate matter 50 from exiting mixing chamber 23. As delivery conduit external section 32 engages with a pressurized-gas source, pressurized-gas is delivered to delivery conduit 30 at delivery conduit inlet 35; the pressurized-gas passes through delivery conduit 30 into discharge conduit 10 to exit micro-abrasive blasting device 75 at discharge conduit outlet 14. Since discharge conduit inlet 12 abuts inlet port 27 the pressurized gas can not enter mixing chamber 23.

Referring to FIG. 4B, a separation gap 45 between the inlet port 27 and discharge conduit inlet 12 is created as discharge conduit 10 is displaced so discharge conduit inlet 12 no longer abuts inlet port 27; As pressurized-gas is supplied to micro-abrasive blasting device 75 through delivery conduit inlet 35, the pressurized-gas flows through delivery conduit 30 and out of inlet port 27, into mixing chamber 23. As flow is initiated, particulate matter 50 instantaneously mixes with the gas-steam within hollow resilient bulb mixing chamber 23 and the powder-gas mixture flows through discharge conduit 10 to strike target surface 40.

Another Embodiment

Referring to FIGS. 5A, 5B, 5C, 5D, 5E, a micro-abrasive blasting device 75 may be constructed of a contiguous pipette structure 80 and may operate as embodiments of FIGS. 3 (A-D) and FIGS. 4 (A-B). However, pipette structure 80 of the FIGS. 5 (A-E) embodiment(s) supports a mixing chamber wall 25 constructed to form a hollow spherical bulb mixing chamber 23. The spherical shape of mixing chamber 23 assures a distal separation between the discharge conduit inlet 12 and the particulate matter 50 at all orientations of mixing chamber 23.

Referring to FIG. 6A, when micro-abrasive blasting device 75 is operated in a horizontal orientation, particulate matter 50 is pulled by gravity to the mixing chamber wall 25 at the bottom surface of mixing chamber 23. Therefore, during operation, the spherical configuration of mixing chamber 23 keeps particulate matter 50 distant from discharge conduit inlet 12, thereby maintaining the proper mixing action.

Referring to FIG. 6B, when micro-abrasive blasting device 75 is operated in a vertical orientation, the spherical shape of mixing chamber 23 also assures a distal separation between the discharge conduit inlet 12 and the particulate matter 50 at all mixing chamber 23 orientations. Additionally, the elimination of the delivery conduit internal section—referred to in the embodiment of FIGS. 3 (A-D) as delivery conduit internal section 34—assures that the pressurized gas stream entering mixing chamber 23 at inlet port 27 always directs the pressurized-gas into particulate matter 50 thereby eliminating the potential for back pressure on particulate matter 50. FIG. 6C is simply another view of the micro-abrasive blasting device.

Referring again to FIGS. 5A-5B, a discharge conduit stop 83 is attached to discharge conduit 10 so discharge conduit stop 83 moves with discharge conduit 10 within mixing chamber 23 from inlet port 27 to discharge port 29. Discharge conduit stop 83 provides a mechanical restriction to the displacement of discharge conduit 10 by creating a restriction at inlet port 27 and discharge port 29. When discharge conduit stop 83 abuts inlet port 27, discharge conduit inlet 12 is properly positioned to seal mixing chamber 23. When discharge conduit stop 83 abuts discharge port 29, discharge conduit inlet 12 is properly positioned to form separation gap 45. Discharge conduit stop 83 could be integral to discharge conduit 10 through a flaring or bulging of discharge conduit 10, a component mounted onto discharge conduit 10 via a gluing, swaging, heat-shrinking, or welding process etc., or simply a drop of dispensed glue.

Referring to FIG. 5A, as discharge conduit inlet 12 abuts inlet port 27, discharge conduit stop 83 is positioned at inlet port 27, restricting discharge conduit inlet 12 from protruding too deep through inlet port 27. Discharge conduit stop 83 may locate discharge conduit inlet 12 within inlet port 27 such that potential liquid residue smoothly passes through micro-abrasive blasting device 75.

Referring to FIG. 5B, discharge conduit 10 is displaced so discharge conduit inlet 12 no longer abuts inlet port 27. The displacement of discharge conduit 10 is restricted by the movement of discharge conduit stop 83 to discharge port 29. Discharge conduit stop 83 may locate discharge conduit inlet 12 at the geometrical center of spherical mixing chamber 23.

FIGS. 5C and 5D illustrate alternatives to the moveable discharge conduit performing sealing, as shown in FIGS. 5A and 5B. Referring to FIG. 5C, a removable closure element 36 which may be in the form of a plug or a cap may be disposed in or on the open distal (from the mixing chamber) end of the delivery conduit 30, sealing it, to prevent abrasive material from escaping during shipping and handling Likewise, a removable closure element 15 which may be in the form of a cap or plug may be disposed on or in the open distal (from the mixing chamber) end of the discharge conduit 30, sealing it, to prevent abrasive material from escaping during shipping and handling. Prior to use, the end plugs/caps 36 and 15 would be removed. In this removable closure element (caps or plugs) embodiment, the discharge conduit 10 need not be moveable, in which case the stop 83 (see FIGS. 5A, 5B) would not be required. If desired, the discharge conduit 10 could nevertheless be movable in the aforementioned manner of FIGS. 5A, 5B to additionally seal the abrasive material 50 in the mixing chamber 23, or simply to make the discharge conduit retractable for shipping and extendable in use.

FIG. 5D illustrates another alternative to the moveable discharge conduit performing sealing, as shown in FIGS. 5A and 5B. Here, an elongate rod 31 extends through the delivery conduit 30. The rod 36 may fit snugly through the delivery conduit outlet 37, and extend sufficiently beyond the outlet 37 so that an end of the rod 31 closes off the discharge conduit inlet 12, thereby sealing abrasive material 50 in the mixing chamber 23. Prior to use, the rod 31 would be removed (withdrawn). In this elongate rod embodiment, the discharge conduit need not be moveable, in which case the stop 83 would not be required. If desired, the discharge conduit 10 could nevertheless be movable in the aforementioned manner of FIGS. 5A, 5B to additionally seal the abrasive material 50 in the mixing chamber 23, or simply to make the discharge conduit retractable for shipping and extendable in use.

Figure 5E:
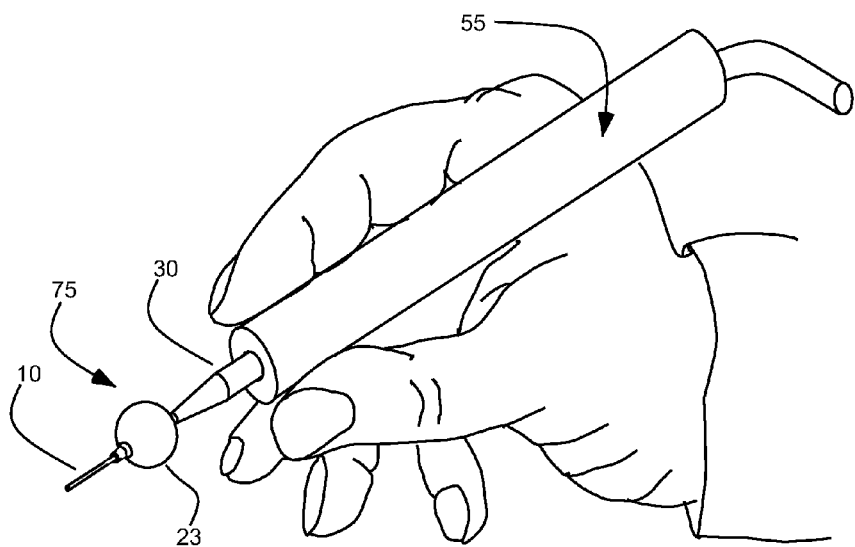
FIG. 5E is a perspective view showing a micro-abrasive blasting device in use, according to an embodiment of the invention.

Referring to FIG. 5E, which may be based on any of the embodiments described with respect to FIGS. 5A, 5B, 5C 5D, the extension of delivery conduit 30 external to the mixing chamber 23 facilitates a more narrow connection to the air abrasion device via a handheld pressurized-gas supply connector 55. Whereas, prior art devices connect to the mixing chamber body, this embodiment connects to a narrower delivery conduit 30. Therefore, the micro-abrasive blasting device 75 may be mounted as a disposable tip onto a non-disposable handheld supply connector 55. While handheld supply connector 55 is held by the user's fingertips, delivery conduit 30 of micro-abrasive blasting device 75 mounts into handheld supply connector 55 downstream of the user's fingertips. Because the innovative micro-abrasive blasting device 75 does not support the user's grip and bulky supply connector, micro-abrasive blasting device 75 can be made shorter and of less rigid material. This configuration greatly decreases the complexity and cost of the micro-abrasive blasting device 75.

Some Other Embodiments

Referring to FIGS. 7A, 7B, contiguous pipette structure 80 is extended to include an additional hollow bulb section to form a discharge conduit bearing 82. The discharge conduit bearing 82 is a tubular extension of the discharge port 29 section, elongated from a capped position end 95 to a mixing position end 97 with a diameter equal to or greater than discharge conduit 10. Discharge conduit bearing 82 provides mechanical support to discharge conduit 10, to assure discharge conduit 10 properly displaces away from inlet port 27; a discharge conduit stop 83 is attached to discharge conduit 10 so discharge conduit stop 83 moves with discharge conduit 10 within discharge conduit bearing 82 from the capped position end 95 to the mixing position end 97. Discharge conduit stop 83 in conjunction with discharge conduit bearing 82 provides a mechanical restriction to the displacement of discharge conduit 10. When discharge conduit stop 83 abuts capped position end 95, discharge conduit inlet 12 is properly positioned to seal mixing chamber 23. When discharge conduit stop 83 abuts mixing position end 97, discharge conduit inlet 12 is properly positioned to form separation gap 45.

Figure 8:
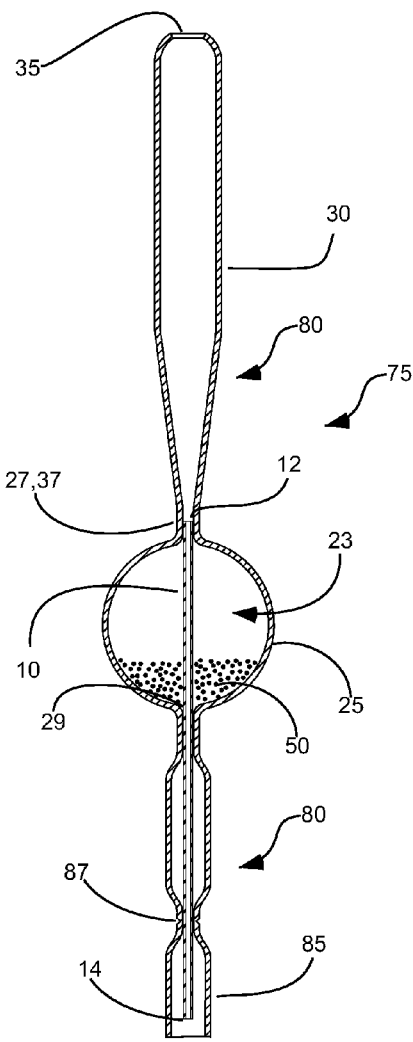
FIG. 8 and FIG. 9 are cross-sectional views of an embodiment of the micro-abrasive blasting device with an integrated protective nozzle guard and integrated particle deflector integral to the pipette structure.

Referring to FIG. 8, contiguous pipette structure 80 is extended to include a protective nozzle guard 85. Protective nozzle guard 85 is constructed by extending pipette structure 80 so it encompasses discharge conduit outlet 14, thereby providing protection to discharge conduit 10 external to mixing chamber 23. Protection of the delivery conduit is important to prevent damage to the delivery conduit during shipping and from the delivery conduit puncturing other surrounding devices in bulk packaging. Nozzle guard 85 also prevents the delivery conduit from sticking the user when mounting micro-abrasive blasting device 75 onto the pressurized-gas connector.

Protective nozzle guard 85 may be removed prior to use, by pulling protective nozzle guard 85 coaxially to discharge conduit 10, thereby fully exposing discharge conduit 10. A perforation to pipette structure 80 may be provided at nozzle guard separation point 87 as to weaken pipette structure 80 at nozzle guard separation point 87. Pulling on protective nozzle guard 85 coaxially to discharge conduit 10, causes pipette structure 80 to separate at nozzle guard separation point 87 allowing the removal of protective nozzle guard 85 to expose discharge conduit 10.

Figure 9:
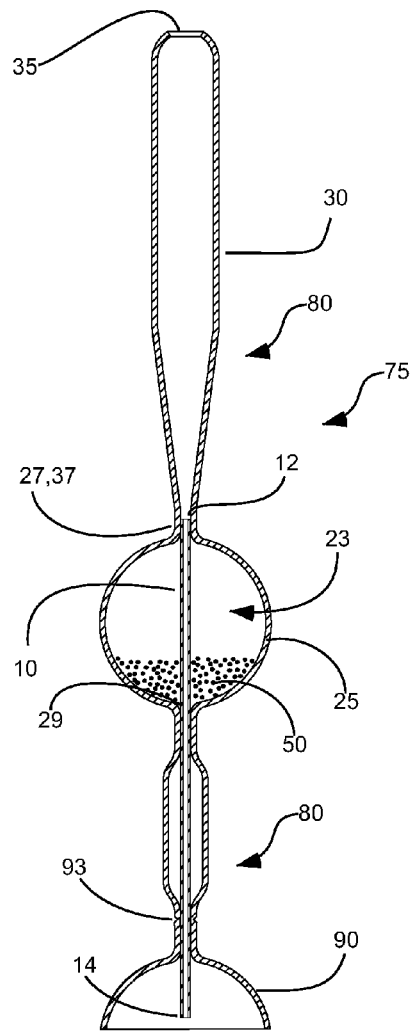

Referring to FIG. 9, contiguous pipette structure 80 is extended to include a portion of a hollow bulb section to form a particle deflector 90. Particle deflector 90 is constructed by extending pipette structure 80 to form a semi-spherical bulb structure. Particle deflector 90 is positioned on discharge conduit 10 as to deflect particulate matter 50 ricocheting off the target surface during use.

Perforation to pipette structure 80 may be provided at particle deflector separation point 93 as to weaken pipette structure 80 at particle deflector separation point 93. Pulling particle deflector 90 coaxially to discharge conduit 10, separates particle deflector 90 at particle deflector separation point 93 to permit the movement of particle deflector 90 along discharge conduit 10. Particle deflector 90 may be positioned near discharge conduit outlet 14 as to deflect particulate matter 50 ricocheting off the target surface during use. The pipette structure 80 may be constructed to include both protective nozzle guard 85 and particle deflector 90.

Mixing Method

Referring to FIG. 3C, a separation gap 45 between the delivery conduit outlet 37 and discharge conduit inlet 12 generates rapidly expanding and contracting gas-stream that forms a pressure gradient 48. The rapid expansion of the gas-stream occurs as the gas-stream exits the narrow delivery conduit outlet 37 and expands into the wider mixing chamber 23. The rapid contraction of the gas-stream occurs as the gas-stream flows from the wider mixing chamber 23 into the narrower discharge conduit inlet 12. Because mixing chamber 23 is a closed-system, the volumetric flow rate into mixing chamber 23 must equal the volumetric flow rate out of mixing chamber 23. Expansion and contraction of the gas-stream across separation gap 45 is accompanied by a localized pressure gradient 48 at separation gap 45. The pressure gradient 48 across separation gap 45 within mixing chamber 23 agitates particulate matter 50 causing particulate matter 50 to aerate. The aerated particulate matter 50 particles are pulled into the gas-stream at separation gap 45, generating an abrasive laden gas stream into discharge conduit inlet 12 and out of discharge conduit outlet 14. Because pressure gradient 48 across separation gap 45 is independent of mixing chamber 23 orientations, agitation also is independent of the orientation of mixing chamber 23.

This mixing method is independent of the mixing chamber shape as long as the mixing chamber 23 is wider than the delivery conduit outlet 37 and discharge conduit inlet 12. In the absence of delivery conduit outlet 37 where delivery conduit 30 terminates at inlet port 27, this innovative mixing method still applies as pressure gradient 48 is formed across separation gap 45. Since separation gap 45 controls the rapidness by which the gas-stream expands and contracts, the distance of separation gap 45 controls the agitation rate of particulate matter 50 within mixing chamber 23. Therefore, the quantity of particulate matter 50 introduced into the gas-steam is selectable by the position of discharge conduit inlet 12 with respect to delivery conduit outlet 37 or inlet port 27.

Some Additional Embodiments

In some of the embodiments disclosed herein, a micro-abrasive device (75) comprises a mixing chamber (23) for containing a supply of abrasive particulate matter (50) an inlet port (27) disposed at one end of the mixing chamber, and a discharge port (29) disposed at an opposite end of the mixing chamber.

A delivery conduit (30) is elongate, has a portion (32) external to the mixing chamber (23), and may have a portion (34) internal to the mixing chamber terminating in an outlet (37), and essentially passes through the inlet port (27). (See FIGS. 3A, 3B) Alternatively, the delivery conduit (30) may terminate at the inlet port (27) without having an internal portion. (See FIGS. 4A, 4B.) In use, the delivery conduit (30) is at the "user end" (or "back end") of the mixing chamber (23), and the device (75) mounts to a handheld supply connector (55) which may be grasped by the user so that the device is positioned downstream of the user's fingertips A discharge conduit (10) is elongate, has a portion internal to the mixing chamber (23) terminating in a discharge conduit inlet (12), may be moveable, essentially passes through the discharge port (29) and has an portion external to the mixing chamber (23) terminating in an outlet (14). In use, the discharge conduit (10) is at the "patient end (or "front end") of the mixing chamber (23).

In many of the embodiments disclosed herein, the discharge conduit (10) is moveable from a "sealed" position with the discharge conduit inlet (12) abutting the delivery conduit outlet (37) so that pressurized gas can not enter mixing chamber (23), thereby sealing abrasive material (50) within the mixing chamber (23), such as after manufacturing, for shipping, and before use. In use, the user may pull the discharge conduit (10) outward, thereby distancing the discharge conduit inlet (12) from the delivery conduit outlet (37) and unsealing the device, thereby permitting pressurized gas to flow into the mixing chamber (23) for agitating the abrasive material for delivery via the delivery conduit (30).

This application claims benefit of Ser. No. 13/083,532 filed Apr. 9, 2011 which is a continuation of Ser. No. 12/764,939 filed Apr. 21, 2010 (U.S. Pat. No. 7,927,188) which is a division of Ser. No. 11/077,098 filed Mar. 10, 2005 (U.S. Pat. No. 7,731,570), all by Groman, incorporated by reference herein. Some features disclosed therein may be incorporated into the embodiments of the device(s) disclosed herein, for example, but not limited to . . .

providing multiple delivery conduits (25) having different apertures providing multiple delivery conduits (25) having different lengths providing the gas-receiving port (39) and the discharge port (45) in the same end wall of the mixing chamber (23)

selecting the length of the delivery conduit (25) and consequent position of the deliver conduit (27) relative the abrasive material to maintain a consistent gas flow perturbation onto the abrasive powder.

Some additional embodiments of the invention (some of which may have been disclosed or fairly implied in U.S. Pat. Nos. 7,731,570 or 7,927,188) will now be described, such as

- providing an inlet port (27) and a discharge port (29) at the same end of the mixing chamber. In the device of U.S. Pat. Nos. 7,731,570 or 7,927,188, the inlet and outlet ports are both disposed in the back (user) end of the mixing chamber. In contrast therewith, in some embodiments of the device disclosed herein, the inlet and discharge ports are both disposed in the front (patient) end of the mixing chamber.
- arranging the delivery conduit which commences at the back (user) end of the mixing chamber to wrap around (pass along side of) the mixing chamber, entering the mixing chamber at the front (patient) end thereof.
- as in U.S. Pat. No. 7,607,972, the discharge conduit may be moveable to alternately seal and unseal the mixing chamber (allowing or preventing gas flow through the device). In U.S. Pat. No. 7,607,972, pulling the discharge conduit "out" from the mixing chamber will unseal the device. (Since the device is intended to be disposable, it is not anticipated that the pulled-out discharge conduit would be pushed back in to re-seal the device.) As disclosed herein, with both of the inlet port (27) and discharge port (29) disposed at the same end of the device, an internal portion of the delivery conduit may be U-shaped, and pushing the discharge conduit "into" the mixing chamber may unseal the device.
- an alternate configuration disclosed herein comprises providing an inlet port (27) and a discharge port (29) at opposite ends of the mixing chamber (as in most of the embodiments shown herein), but rather than the discharge conduit (10) being moveable to seal and unseal the device, the delivery conduit (30) is moveable to seal and unseal the device.

Both Ports at the Same (Front, Patient) End

FIGS. 10A, 10B disclose an embodiment or configuration of the micro-abrasive blasting device 75 generally comprising:

- a mixing chamber 23 for containing a supply of abrasive particulate matter (50, not shown) and having two ends—a "user end" 23*a* and a "patient end" 23*b;*
- an inlet port 27 disposed at the patient end 23*b* of the mixing chamber 23; and
- a discharge port 29 disposed at the patient end 23*b* (the same one of the two ends of the mixing chamber).

A delivery conduit 30 is elongate, situated external to the mixing chamber 23 along side of the mixing chamber, and extends from adjacent to (near, but not in fluid communication with) the user end 23*a* of the mixing chamber 23 to the patient end 23*b* of the mixing chamber 23. At the user end (of the device), the delivery conduit 30 may extend further, terminating (or originating) at a delivery conduit inlet 35 for receiving pressurized gas from a supply (not shown). At the patient end 23*b* of the mixing chamber 23, the delivery conduit 30 terminates at a delivery conduit outlet 37 which is essentially coincident (contiguous) with the inlet port 27 of the mixing chamber 23.

A discharge conduit 10 is elongate, has a portion 11 internal to the mixing chamber 23 terminating in a discharge conduit inlet 12, may be moveable, essentially passes through the discharge port 29 of the mixing chamber 23 and has a portion 13 external to the mixing chamber 23 terminating in a discharge conduit outlet 14.

In many of the embodiments disclosed herein, the discharge conduit 10 is moveable from a "sealed" position with the discharge conduit inlet 12 abutting the delivery conduit outlet 37 so that pressurized gas can not enter mixing chamber 23. Unlike some of the previous embodiments (such as FIGS. 4A, 4B, 4C), where the inlet port 27 and discharge port 29 are disposed at opposite ends of the mixing chamber 23, in the embodiment of FIGS. 10A, 10B, both the inlet port 27 and the discharge port 29 are located at the same end 23*b* of the mixing chamber 23. To facilitate this configuration, the internal portion 11 of the discharge conduit may be U-shaped, making a substantially 180-degree turn so as to be oriented towards the patient end 23*b* of the mixing chamber.

FIG. 10A shows the device 75 with the discharge conduit inlet 12 abutting the delivery inlet port 27 (delivery conduit outlet 37)—this is the "closed" or "sealed" position—and gas is prevented from flowing through the device. (Abrasive material 50 within the mixing chamber 23 is omitted, for illustrative clarity.) The device 75 may be shipped in this "sealed" configuration, so that abrasive material does not leak out during shipping. Caps and plugs, as described with respect to FIG. 5C may be added to this (or other) embodiments.

FIG. 10B shows the device 75 with the discharge conduit inlet 12 displaced from the delivery inlet port 27 (delivery conduit outlet 37)—this is the "open" or "unsealed" position—and gas may flow through the device. (Abrasive material within the mixing chamber is omitted, for illustrative clarity.) The device 75 may be unsealed by the user, by pushing the discharge conduit 10 inward (to the right, as illustrated), thereby allowing gas to flow into the delivery conduit inlet 35, through the delivery conduit 30, into the mixing chamber 23 and perturbating abrasive material (50) which will be delivered to a target (such as patient's tooth) via the discharge conduit 10 out of the discharge conduit outlet 14.

Benefits of this configuration may include . . .

- the overall device 75 becomes shorter when the discharge conduit 10 is unseated (pushed in to unseal the mixing chamber), which may provide more precise aim and positioning for the user (dentist, dental tech)
- the ability to contain more powder/particulate material (50) while keeping the overall device length shorter
- the movable discharge conduit 10 may abut the device wall during operation, thereby providing resistance to movement during operation
- the shape of the discharge conduit 10 may eliminate the need for a stop or protrusion (83)—in other words, it may not be pushed in too far. (Contrast this with the pulling out embodiments which comprise a stop, such as in FIGS. 5A, 5B, to prevent pulling the discharge conduit completely out.)
- the air flow from the delivery conduit wall inlet port 27 (and end 37 of delivery conduit 30) may eliminate the need for an inlet conduit (34) since the air flow is from the bottom side (end). This is another example of the delivery conduit 30 ending at the gas inlet port 27, without extending (as an inlet conduit) into the chamber.

Various Configurations, Illustrated Schematically

FIG. 11A illustrates, schematically, a micro-abrasive blasting device (75) comprising a mixing chamber (23), a delivery conduit (30) extending from one end (user end) of the mixing chamber (inlet port 27 omitted, for illustrative clarity), a discharge conduit (10) extending through an opposite end (patient end) of the mixing chamber (discharge port 29 omitted, for illustrative clarity) and having a portion (11) internal to the mixing chamber. Abrasive material (50) is omitted, for illustrative clarity. The discharge conduit (10) may be pulled, outward from the mixing chamber, to unseal (open) the device. Compare FIGS. 4A, 4B. This represents a device configuration having inlet and discharge ports at opposite ends of the mixing chamber, and pull (the discharge conduit) to open.

Figure 10A:
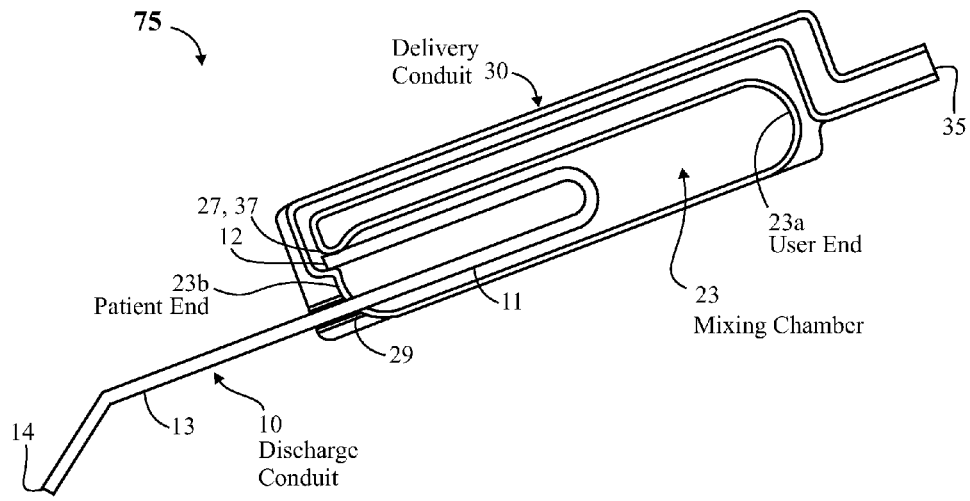
FIGS. 10A and 10B are cross-sectional views of an embodiment of the micro-abrasive blasting device, according to an embodiment of the invention.
Figure 10B:
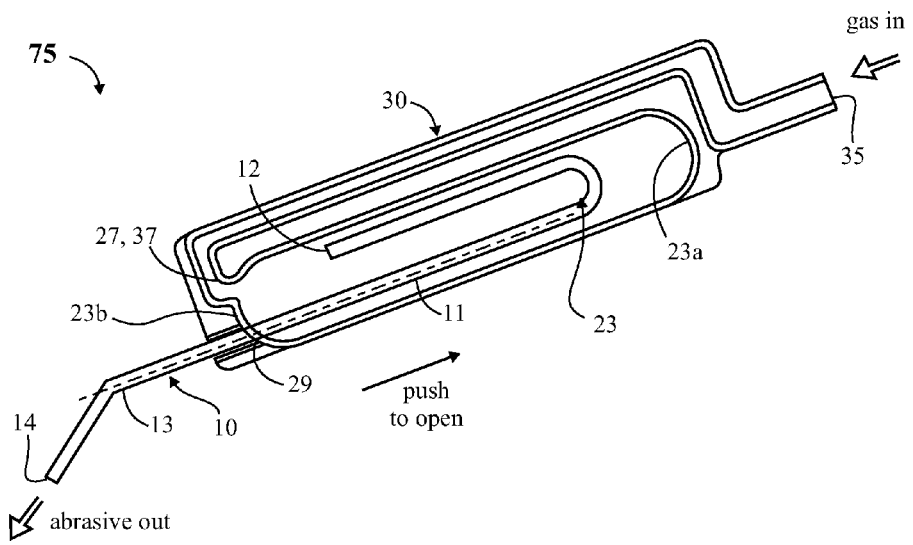
Figure 11A:
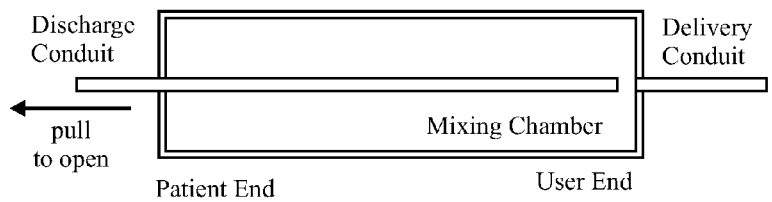
FIGS. 11A, 11B, 11C, 11D are cross-sectional schematic representations of micro-abrasive blasting device, according to some embodiments of the invention.
Figure 11B:
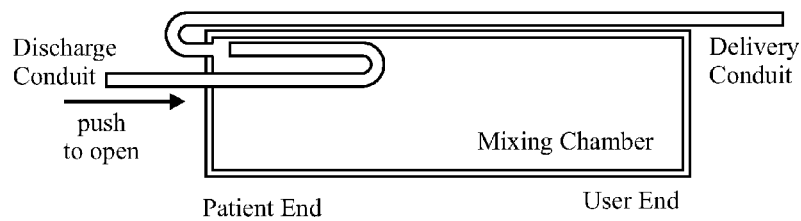

FIG. 11B illustrates, schematically, a micro-abrasive blasting device (75) comprising a mixing chamber (23), a delivery conduit (30) extending from a user end of the overall device (adjacent the user end of the mixing chamber), alongside of the mixing chamber, making a "U-turn" and connecting to the patient end of the mixing chamber (inlet port 27 omitted, for illustrative clarity), a discharge conduit (10) extending from the same (patient) end of the mixing chamber (discharge port 29 omitted, for illustrative clarity) and having a U-shaped portion (11) internal to the mixing chamber. Abrasive material (50) is omitted, for illustrative clarity. The discharge conduit (10) may be pushed, inward into the mixing chamber, to unseal (open) the device. Compare FIGS. 10A, 10B. This represents a device configuration having inlet and discharge ports at the same (patient) end of the mixing chamber, and push (the discharge conduit) to open.

Figure 11C:

FIG. 11C illustrates, schematically, a micro-abrasive blasting device (75) comprising a mixing chamber (23), a delivery conduit (30) extending from one end (user end) of the mixing chamber (inlet port 27 omitted, for illustrative clarity), a discharge conduit (10) extending from the same (user) end of the mixing chamber (discharge port 29 omitted, for illustrative clarity) and making a "U-turn" and extending alongside of the mixing chamber to beyond the opposite (patient) end of the mixing chamber. Abrasive material (50) is omitted, for illustrative clarity. The delivery conduit (10) may be moved, inward and outward from the mixing chamber, to control the perturbation of abrasive material in the mixing chamber. Compare FIGS. 4A-4C of U.S. Pat. No. 7,731,570. This represents a device configuration having inlet and discharge ports at the same (user) end of the mixing chamber, and also a feature that the delivery conduit is moveable in and out of the mixing chamber to control perturbation.

Figure 11D:
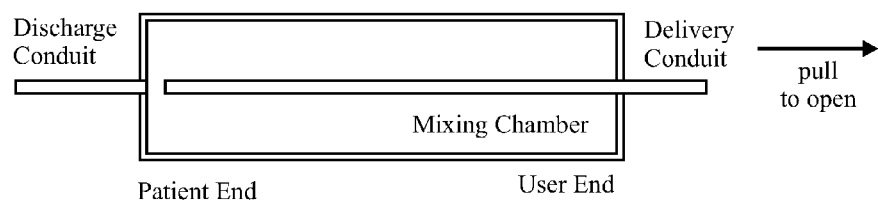

FIG. 11D illustrates, schematically, a micro-abrasive blasting device (75) comprising a mixing chamber (23), a delivery conduit (30) extending into one end (user end) of the mixing chamber (inlet port 27 omitted, for illustrative clarity) and having a portion within the mixing chamber, and a discharge conduit (10) extending from an opposite end (patient end) of the mixing chamber (discharge port 29 omitted, for illustrative clarity). Abrasive material (50) is omitted, for illustrative clarity. The delivery conduit (30) may be pulled, outward from the mixing chamber, to unseal (open) the device. Contrast FIG. 11A (this is the "opposite" of FIG. 11A). This represents a device configuration having inlet and discharge ports at opposite ends of the mixing chamber, and pull (the delivery conduit) to open.

Summary of Claims from parent application Ser. No. 11/452,467 Filed Jun. 13, 2006

The following are representative of claims from the parent patent application.

A micro-abrasive blasting device may comprise:
a chamber having a chamber wall and a hollow interior;
a inlet port in said chamber wall;
a discharge port in the chamber wall;
a delivery conduit elongated from a delivery conduit inlet external to said chamber to a delivery conduit outlet disposed within the chamber and extending in fluid communications through said inlet port;
a discharge conduit elongated from a discharge conduit inlet internal to the chamber to a discharge conduit outlet external to the chamber and extending in fluid communications through said discharge port;
a quantity of particulate matter disposed within said chamber; wherein a handheld pressurized-gas supply connector mounts to said delivery conduit external to the chamber.

Pressurized-gas supplied to delivery conduit inlet may pass through the delivery conduit outlet into the chamber to generate an abrasive laden gas stream out of said discharge conduit.

Said discharge conduit inlet may abut delivery conduit outlet to seal said particulate matter within said chamber.

Pressurized-gas supplied to delivery conduit inlet passes through the delivery conduit and discharge conduit without entering the chamber.

Displacement of said discharge conduit inlet away from delivery conduit outlet may unseal the chamber to allow pressurized-gas flow through the chamber to generate an abrasive laden gas stream.

The delivery conduit outlet may terminates at the inlet port of said chamber.

The chamber may be spherical.

A discharge conduit stop may be mounted to said discharge conduit is disposed within the mixing chamber to restrict the movement range of the discharge conduit.

A pre-filled disposable pipette structure for micro-abrasive blasting device may comprise:
a hollow tubular pipette structure;
said pipette structure having a hollow bulb section forming a mixing chamber;
said pipette structure further having a open ended hollow tubular delivery section smaller in diameter and contiguous with the bulb section, for delivery of pressurized-gas;
said pipette structure also having a hollow tubular discharge section smaller in diameter and contiguous with the bulb section, for discharging abrasive laden gas stream;
a quantity of particulate matter disposed within said mixing chamber;
a discharge conduit elongated from a discharge conduit inlet to a discharge conduit outlet;
wherein said discharge conduit is mounted in fluid communications through said discharge section of said pipette structure so said discharge conduit inlet is internal to the mixing chamber and discharge conduit outlet is external to the mixing chamber.

A pressurized-gas connector may mount to said delivery section.

Pressurized-gas supplied to delivery section may pass through the delivery conduit outlet into the chamber to generate an abrasive laden gas stream out of said discharge conduit.

The discharge conduit inlet may abut delivery section to seal said particulate matter within said mixing chamber.

Pressurized-gas delivered to delivery section may pass through the delivery section and discharge conduit without entering the mixing chamber.

Displacement of said discharge conduit inlet away from delivery section may unseal the mixing chamber to allow pressurized-gas flow through the mixing chamber to generate an abrasive laden gas stream.

The pipette structure may be constructed of a thermoplastic material selected from a group consisting of: polycarbonate, polyethylene, polyester, polystyrene, polypropylene, polysulfone, polyurethane, or ethylene-vinyl-acetate.

The pipette structure may be formed by extrusion blow molding in a two-piece mold.

The pipette structure may be formed by thermoforming a plastic tube.

The mixing chamber may be spherical.

The may be hollow tubular delivery section may be extended internal to said mixing chamber.

The pipette's hollow structure may be configured in cross section as selected from a group consisting of round, oval, square, rectangular and polygonal shapes.

The pipette's bulb section may have a cylindrical configuration with each end having a cone-shaped taper interfacing on one end with the delivery tube section, and on the other end with the discharge tubular section.

A method of using a handheld gas supply connector with a device for propelling particulate matter may comprise the steps of:
  placing particulate matter within a mixing chamber, said mixing chamber comprising a mixing chamber wall, a inlet port at a one end of the chamber and a discharge port at an opposite end of the chamber and sized for completing at least one dental procedure;
  extending a gas delivery conduit disposed external to the mixing chamber in fluid communications through said inlet port into the mixing chamber to terminate at a delivery conduit outlet;
  holding a pressurized-gas supply connector in a manner by grasping said supply connector between two fingers of one hand during the application of said device for at least one dental procedure;
  mounting said gas delivery conduit external to the chamber to said handheld supply connector whereby the mixing chamber is downstream of the fingers grasping location;
  applying gas flow through the gas delivery conduit into the mixing chamber;
  discharging a mixture of gas flow and said particulate matter through a discharge conduit in said discharge port for abrading at least one target surface of a dental procedure.

The delivery conduit outlet may terminate at said inlet port of the mixing chamber.

A method of sealing particulate matter within a device for propelling particulate matter may comprise the steps of:
  placing particulate matter within a mixing chamber, said mixing chamber comprising a mixing chamber wall, a inlet port at a one end of the chamber and a discharge port at an opposite end of the chamber and sized for completing at least one dental procedure;
  extending a gas delivery conduit disposed external to the mixing chamber in fluid communications through said inlet port into the mixing chamber to terminate at a delivery conduit outlet;
  inserting a discharge conduit in fluid communication through said discharge port extending from a discharge conduit inlet internal to said chamber to a discharge conduit outlet external to the chamber;
  positioning said discharge conduit inlet to abut said delivery conduit outlet thereby sealing particulate matter within the mixing chamber.

Pressurized-gas supplied to said gas delivery conduit may pass through the delivery conduit and discharge conduit without entering the mixing chamber.

Displacing said discharge conduit inlet away from said delivery conduit outlet may unseal the chamber.

Delivering pressurized-gas to said gas delivery conduit may pass through the delivery conduit outlet into the chamber to generate an abrasive laden gas stream out of said discharge conduit.

The delivery conduit outlet may terminate at said inlet port of the mixing chamber.

A method for generating an abrasive laden gas stream within a micro-abrasive blasting device may comprise the steps of:
  placing particulate matter within a mixing chamber, said mixing chamber comprising a mixing chamber wall, a inlet port at a one end of the chamber and a discharge port at an opposite end of the chamber and sized for completing at least one dental procedure;
  extending a gas delivery conduit disposed external to the mixing chamber in fluid communications through said inlet port into the mixing chamber to terminate at a delivery conduit outlet;
  inserting a discharge conduit in fluid communication through said discharge port extending from a discharge conduit inlet internal to said chamber to a discharge conduit outlet external to the chamber;
  positioning said discharge conduit inlet to have a separation gap with said delivery conduit outlet;
  applying a gas flow through the gas delivery conduit into the mixing chamber whereby forming a pressure gradient across said separation gap;
  aerating said particulate matter to mix with the said gas flow;
  discharging a mixture of gas flow and said particulate matter through a discharge conduit in said discharge port for abrading at least one target surface of a dental procedure.

The delivery conduit outlet may terminate at said inlet port of the mixing chamber.

In addition to the above, the following are disclosed but may not have been claimed in the parent application:

A micro-abrasive blasting device may comprise:
  a chamber having a chamber wall and a hollow interior;
  an inlet port in said chamber wall;
  a discharge port in the chamber wall;
  a tubular delivery conduit section contiguous with said chamber wall elongated from a delivery conduit inlet external to said chamber to a delivery conduit outlet terminating at said inlet port;
  a tubular discharge section contiguous with said chamber wall elongates from said discharge port external to said chamber;
  a discharge conduit elongated from a discharge conduit inlet internal to the chamber to a discharge conduit outlet external to the chamber and extending through said tubular discharge section and in fluid communications with said tubular discharge section;
  a quantity of particulate matter disposed within said chamber;
  wherein a handheld pressurized-gas supply connector mounts to said tubular delivery conduit section external to the chamber;
  wherein:
  a discharge conduit stop mounted to said discharge conduit is disposed external to the mixing chamber to prevent the extraction of the discharge conduit out of the tubular delivery conduit section and tubular discharge section.

A discharge conduit bearing may comprise a elongated tubular extension of the discharge port extending from the mixing chamber, a portion of which has a diameter equal to or greater than the discharge conduit;

wherein the discharge conduit stop is disposed within the discharge conduit bearing.

A micro-abrasive blasting device may comprise:

a mixing chamber comprising a wall, an inlet port disposed in the wall and a discharge port disposed in the wall;
- a delivery conduit extending from external the mixing chamber to the inlet port;
- a discharge conduit extending from internal the mixing chamber, through the discharge port, to external the mixing chamber, and having a discharge conduit inlet disposed within the mixing chamber; and
- a discharge conduit bearing comprising a elongated tubular extension of the discharge port extending from the mixing chamber, a portion of which has a diameter equal to or greater than the discharge conduit;

wherein the discharge conduit stop is disposed within the discharge conduit bearing.

A micro-abrasive blasting device may comprise:

a mixing chamber comprising a wall, an inlet port disposed in the wall and a discharge port disposed in the wall;
- a delivery conduit extending from external the mixing chamber through the inlet port to within the mixing chamber; and
- a discharge conduit extending from internal the mixing chamber, through the discharge port, to external the mixing chamber, and having a discharge conduit inlet disposed within the mixing chamber.

The delivery conduit may extend to within the mixing chamber.

A micro-abrasive blasting device may comprise:

a mixing chamber comprising a wall, an inlet port disposed in the wall and a discharge port disposed in the wall;
- a delivery conduit extending from external the mixing chamber to the inlet port;
- a discharge conduit extending from internal the mixing chamber, through the discharge port, to external the mixing chamber, having a discharge conduit inlet disposed within the mixing chamber, and having a portion including a discharge conduit outlet disposed external the mixing chamber; and
- a protective nozzle guard extending from the mixing chamber and encompassing the discharge conduit outlet A particle deflector may be positioned on the discharge conduit, in the form of a semi-spherical bulb structure, for deflecting particulate matter ricocheting off a target surface during use.

A micro-abrasive blasting device may comprise:

a mixing chamber comprising a wall, an inlet port disposed in the wall and a discharge port disposed in the wall;
- a delivery conduit extending from external the mixing chamber to the inlet port;

a discharge conduit extending from internal the mixing chamber, through the discharge port, to external the mixing chamber, and having a discharge conduit inlet disposed within the mixing chamber; and
- a particle deflector positioned on the discharge conduit, in the form of a semi-spherical bulb structure, for deflecting particulate matter ricocheting off a target surface during use.

Advantages

From the description(s) above, the following advantages may become evident:

(a) Use of the delivery conduit to seal the mixing chamber, thereby:
1. reducing the component count; and
2. making disposable pipette structure usable for air abrasion applications.

(b) Use the delivery conduit to create a bypass to the mixing chamber, thereby eliminating liquid entrapment within the mixing chamber.

(c) Extending the delivery conduit external to the mixing chamber, thereby making the device adaptable to a handheld gas supply connector and standard tube fitting.

(d) Generation of a localized pressure gradient within the mixing chamber to generate and control powder agitation rates.

(e) Use of a spherical mixing chamber to deliver consistent powder perturbation at all mixing chamber orientations.

(f) Simplified construction using contiguous pipette structure fabricated to form the body of the micro-abrasion device.

(g) the "push to open" feature (FIG. 10) allows for a shorter discharge conduit

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

Summary, Ramification, and Scope

The present invention may accomplish the above-stated objectives, as well as others, as may be determined by a fair reading and interpretation of the entire specification.

Accordingly, the reader will see that the micro-abrasive blasting device may have reduced components, simplified construction, enhanced mixing methodology, and mountable to handheld gas supply connector.

Furthermore, the micro-abrasive blasting device has the additional advantages in that it provides a more narrow pressurized-gas supply connection.

it provides a sealed device that is resistant to fluid contamination.

it provides a reliable device that delivers a consistent quantity of abrasive at any orientation.

it provides the user with ability to select powder delivery rates by external manipulation of the discharge conduit position.

it provides a simplified construction methodology which reduces the manufacturing cost of the product.

Thus the scope of the invention should be determined by the appended claims and their legal equivalents, rather than by the examples given.

What is claimed is:

1. A micro-abrasive blasting device, comprising:
- a mixing chamber having a side wall, a first end wall at one end of the chamber and a second end wall at an opposite end of the chamber;
- a quantity of abrasive powder disposed within said mixing chamber;
- a gas-receiving inlet port in one of the first and second end walls;
- a discharge port in the same one of the first and second end walls;
- a delivery conduit extending to the inlet port; and
- a discharge conduit extending through said discharge port from within the mixing chamber to external to the mixing chamber;

wherein:
the discharge conduit is elongate, has a portion internal to the mixing chamber terminating in a discharge conduit inlet, passes through the discharge port of the mixing chamber and has a portion external to the mixing chamber terminating in a discharge conduit outlet;
the portion of the discharge conduit internal to the mixing chamber is U-shaped; and
the discharge conduit is movable, into the mixing chamber, to unseal the device.

2. The micro-abrasive blasting device of claim 1, wherein:
the same end is a patient end of the device.

3. The micro-abrasive blasting device of claim 1, wherein:
the delivery conduit extends external, alongside of the mixing chamber from adjacent the one of the first and second end walls at least to the other, user end of the device.

4. The micro-abrasive blasting device of claim 3, wherein:
the delivery conduit is U-shaped.

5. A method of selectively sealing particulate matter within a device for mixing and propelling particulate matter, the method comprising the steps:
providing a mixing chamber comprising an end wall;
providing a gas-receiving inlet port in the end wall;
providing a discharge port in the end wall;
providing a delivery conduit external to the chamber, extending at least to the inlet port and having a delivery conduit outlet;
providing a discharge conduit elongated from a discharge conduit inlet to a discharge conduit outlet and extending through said discharge port from internal to the chamber to external to the chamber;
positioning the discharge conduit inlet to abut the delivery conduit outlet for selectively sealing particulate matter within the mixing chamber.

6. The method of claim 5 wherein:
the device is unsealed by pulling out the discharge conduit.

7. The method of claim 5 wherein:
the device is unsealed by pushing in the discharge conduit.

8. The method, according to claim 5, wherein:
with the discharge conduit inlet abutting the delivery conduit outlet, pressurized gas supplied to the gas delivery conduit passes through the gas delivery conduit and the discharge conduit without entering the mixing chamber.

9. The method, according to claim 5, further comprising:
displacing the discharge conduit inlet away from the delivery conduit outlet;
wherein with the discharge conduit inlet displaced away from the delivery conduit outlet, pressurized gas supplied to the gas delivery conduit passes through the gas delivery conduit and enters the mixing chamber.

10. The method, according to claim 9, further comprising:
providing particulate matter within the mixing chamber;
supplying pressurized-gas to the gas delivery conduit; and
generating an abrasive-laden gas stream out of said discharge conduit.

11. The method according to claim 5, wherein:
said delivery conduit outlet terminates at the inlet port of the mixing chamber.

12. The method according to claim 5, wherein:
the gas delivery conduit extends through the inlet port into the mixing chamber.

13. The method of claim 5, further comprising:
providing means for preventing extraction of the discharge conduit from the mixing chamber.

14. A method of delivering abrasive material to a patients' tooth, comprising:
providing a micro-abrasive blasting device comprising:
a mixing chamber;
a gas delivery conduit extending from the mixing chamber; and
a discharge conduit extending from the mixing chamber;
providing a handheld pressurized-gas supply connector;
mounting the micro-abrasive blasting device by its gas delivery conduit into the handheld supply connector;
providing particulate matter within the mixing chamber;
supplying pressurized-gas, via the supply connector, to the gas delivery conduit;
holding the supply connector with a user's fingertips so that the mixing chamber is oriented downstream of the user's fingertips; and
pushing the discharge conduit into the mixing chamber to unseal the device.

15. The method of claim 14, wherein:
the gas delivery conduit mounts into the supply connector downstream of the user's fingertips.

16. The method of claim 14, further comprising:
providing particulate matter within the mixing chamber;
supplying pressurized-gas, via the supply connector, to the gas delivery conduit; and
generating an abrasive-laden gas stream out of said discharge conduit.

17. The method of claim 14, further comprising:
applying a gas flow through the gas delivery conduit into the mixing chamber;
aerating said particulate matter to mix with the said gas flow;
discharging a mixture of gas flow and said particulate matter through a discharge conduit in said discharge port for abrading at least one target surface of a dental procedure.

18. The micro-abrasive blasting device of claim 1, wherein:
said discharge conduit inlet abuts said inlet port to prevent particulate matter from exiting the mixing chamber.

19. The micro-abrasive blasting device of claim 1, wherein:
the discharge conduit abuts the same one of the first and second end walls during operation, thereby providing resistance to movement during operation.

* * * * *